(12) United States Patent
Witschel et al.

(10) Patent No.: US 8,445,407 B2
(45) Date of Patent: May 21, 2013

(54) HERBICIDAL TETRAHYDROPHTHALIMIDES

(75) Inventors: Matthias Witschel, Bad Duerkheim (DE); Trevor William Newton, Neustadt (DE); Thomas Seitz, Viernheim (DE); Helmut Walter, Obrigheim (DE); Bernd Sievernich, Hassloch (DE); Anja Simon, Weinheim (DE); Ricarda Niggeweg, Mannheim (DE); Klaus Grossmann, Neuhofen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/505,106

(22) PCT Filed: Oct. 28, 2010

(86) PCT No.: PCT/EP2010/066363
§ 371 (c)(1),
(2), (4) Date: Apr. 30, 2012

(87) PCT Pub. No.: WO2011/051393
PCT Pub. Date: May 5, 2011

(65) Prior Publication Data
US 2012/0214668 A1 Aug. 23, 2012

(30) Foreign Application Priority Data

Nov. 2, 2009 (EP) .................................... 09174774

(51) Int. Cl.
*C07D 413/04* (2006.01)
*A01N 43/04* (2006.01)
(52) U.S. Cl.
USPC .......................................... 504/225; 544/105
(58) Field of Classification Search
USPC .......................................... 544/105; 504/225
See application file for complete search history.

(56) References Cited

U.S. PATENT DOCUMENTS 5,080,710 A * 1/1992 Rueb et al. .................... 504/225

FOREIGN PATENT DOCUMENTS

EP 0 170191 2/1985
WO WO 2010/145992 12/2010

OTHER PUBLICATIONS

International Search Report completed Jan. 14, 2011, in International Application No. PCT/EP2010/066363, filed Oct. 28, 2010.
International Preliminary Report on Patentability dated Jan. 26, 2012, from corresponding International Application No. PCT/EP2010/066363, filed Oct. 28, 2010.

* cited by examiner

*Primary Examiner* — Kahsay T Habte
(74) *Attorney, Agent, or Firm* — Brinks Hofer Gilson & Lione

(57) ABSTRACT

The present invention relates to tetrahydrophthalimides of formula I

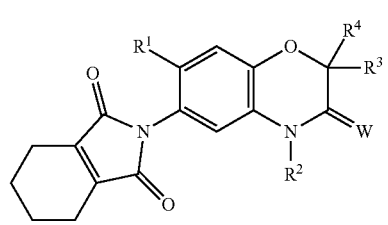

wherein the variables are defined according to the description, processes and intermediates for preparing the benzoxazinones of the formula I, compositions comprising them and their use as herbicides, i.e. for controlling harmful plants, and also a method for controlling unwanted vegetation which comprises allowing a herbicidal effective amount of at least one tetrahydrophthalimide of the formula I to act on plants, their seed and/or their habitat.

20 Claims, No Drawings

HERBICIDAL TETRAHYDROPHTHALIMIDES

This application is a National Stage application of International Application No. PCT/EP2010/066363 filed Oct. 28, 2010, the entire contents of which is hereby incorporated herein by reference. This application also claims priority under 35 U.S.C. §119 to European Patent Application No. 09174774.1, filed Nov. 2, 2009, the entire contents of which is hereby incorporated herein by reference.

The present invention relates to tetrahydrophthalimides of the general formula I defined below and to their use as herbicides. Moreover, the invention relates to compositions for crop protection and to a method for controlling unwanted vegetation.

EP 170191 describes structurally similar compounds for which herbicidal action is stated, which differ from the tetrahydrophthalimides I according to the present invention in that the benzo[1,4]oxazine ring carries in the 2-position preferably one alkyl group, whereas the tetrahydrophthalimides of formula I according to the present invention are substituted in said position by two halogen atoms.

However, the herbicidal properties of these known compounds with regard to the harmful plants are not always entirely satisfactory.

It is therefore an object of the present invention to provide tetrahydrophthalimides having improved herbicidal action. To be provided are in particular tetrahydrophthalimides which have high herbicidal activity, in particular even at low application rates, and which are sufficiently compatible with crop plants for commercial utilization.

These and further objects are achieved by the tetrahydrophthalimides of the formula I, defined below, and by their agriculturally suitable salts.

Accordingly, the present invention provides tetrahydrophthalimides of formula I

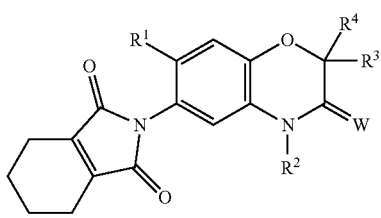

wherein
$R^1$ is hydrogen or halogen;
$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^3$ is halogen;
$R^4$ is halogen, preferably fluorine; and
W is O or S.

The present invention also provides herbicidally active compositions comprising at least one tetrahydrophthalimide of formula I and at least one further compound selected from herbicidal active compounds B and safeners C.

The present invention also provides the use of tetrahydrophthalimides of the general formula I as herbicides, i.e. for controlling harmful plants.

The present invention also provides mixtures comprising at least one tetrahydrophthalimide of the formula I and auxiliaries customary for formulating crop protection agents.

The present invention furthermore provides a method for controlling unwanted vegetation where a herbicidal effective amount of at least one tetrahydrophthalimide of the formula I is allowed to act on plants, their seeds and/or their habitat. Application can be done before, during and/or after the emergence of the undesirable plants.

Moreover, the invention relates to processes and intermediates for preparing tetrahydrophthalimides of the formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the tetrahydrophthalimides of formula I as described herein are capable of forming geometrical isomers, for example E/Z isomers, it is possible to use both, the pure isomers and mixtures thereof, in the compositions according to the invention.

If the tetrahydrophthalimides of formula I as described herein have one or more centers of chirality and, as a consequence, are present as enantiomers or diastereomers, it is possible to use both the pure enantiomers and diastereomers and their mixtures in the compositions according to the invention.

The organic moieties mentioned in the definition of the variables $R^1$ to $R^4$ are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:
$C_1$-$C_4$-alkyl and also the $C_1$-$C_4$-alkyl moieties of $C_3$-$C_6$-cycloalkyl-$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-alkyoxy-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2- dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and trisdecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxycarbonyl-$C_1$-$C_4$-alkoxy: $C_1$-$C_4$-alkoxy as mentioned above, and also, for example, pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy.

The preferred embodiments of the invention mentioned herein below have to be understood as being preferred either independently from each other or in combination with one another.

According to a preferred embodiment of the invention preference is also given to those tetrahydrophthalimides of formula I, wherein the variables, either independently of one another or in combination with one another, have the following meanings:

$R^1$ is hydrogen;
is also preferably halogen, particularly preferred F or Cl, especially preferred F;

$R^2$ is $C_3$-$C_6$-alkynyl or $C_3$-$C_6$-halolkynyl, preferably $C_3$-alkynyl or $C_3$-halolkynyl, particularly preferred $CH_2C\equiv CH$, $CH_2C\equiv CCl$ or $CH_2C\equiv CBr$;
is also preferably $C_3$-$C_6$-alkynyl or $C_3$-$C_6$-cycloalkyl-$C_1$-$C_6$-alkyl, particularly preferred propargyl or cyclopropylmethyl;
is also preferably $C_3$-$C_6$-alkynyl, preferably $C_3$-alkynyl; particularly preferred $CH_2C\equiv CH$;
is also preferably $C_3$-$C_6$-haloalkynyl, preferably $C_3$-haloalkynyl, particularly preferred $CH_2C\equiv CCl$ or $CH_2C\equiv CBr$;

$R^3$ is F;

$R^4$ is F;

W is O,
is also preferably S.

Particular preference is given to tetrahydrophthalimides of formula I, wherein $R^4$ is F and W is O and which herein below are also referred to as tetrahydrophthalimides of formula Ia:

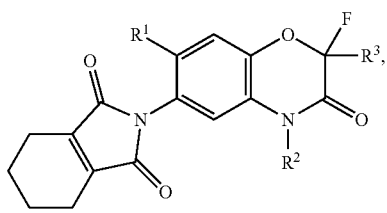

wherein the variables $R^1$, $R^2$ and $R^3$ have the meanings, in particular the preferred meanings, as defined above.

Special preference is given to tetrahydrophthalimides of the formulae Ia1 to Ia30 of table A, where the definitions of the variables $R^1$, $R^2$ and $R^3$ are of particular importance for the compounds according to the invention not only in combination with one another but in each case also on their own:

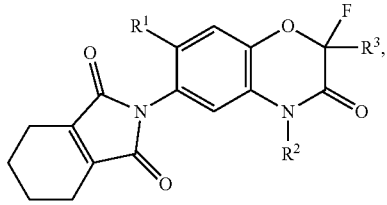

TABLE A

| no. | $R^1$ | $R^2$ | $R^3$ |
| --- | --- | --- | --- |
| Ia1 | H | H | F |
| Ia2 | H | $CH_3$ | F |
| Ia3 | H | $C_2H_5$ | F |
| Ia4 | H | $CH_2$—$C_2H_5$ | F |
| Ia5 | H | $CH(CH_3)_2$ | F |
| Ia6 | H | $CH_2$—$CH_2$—$(CH_3)_2$ | F |
| Ia7 | H | $CH_2$—$CH$=$CH_2$ | F |
| Ia8 | H | $CH_2C\equiv CH$ | F |
| Ia9 | H | $CH_2C\equiv C$—Cl | F |
| Ia10 | H | $CH_2C\equiv C$—Br | F |
| Ia11 | F | H | F |
| Ia12 | F | $CH_3$ | F |
| Ia13 | F | $C_2H_5$ | F |
| Ia14 | F | $CH_2$—$C_2H_5$ | F |
| Ia15 | F | $CH(CH_3)_2$ | F |
| Ia16 | F | $CH_2$—$CH_2$—$(CH_3)_2$ | F |
| Ia17 | F | $CH_2$—$CH$=$CH_2$ | F |
| Ia18 | F | $CH_2C\equiv CH$ | F |
| Ia19 | F | $CH_2C\equiv C$—Cl | F |
| Ia20 | F | $CH_2C\equiv C$—Br | F |
| Ia21 | Cl | H | F |
| Ia22 | Cl | $CH_3$ | F |
| Ia23 | Cl | $C_2H_5$ | F |
| Ia24 | Cl | $CH_2$—$C_2H_5$ | F |
| Ia25 | Cl | $CH(CH_3)_2$ | F |
| Ia26 | Cl | $CH_2$—$CH_2$—$(CH_3)_2$ | F |
| Ia27 | Cl | $CH_2$—$CH$=$CH_2$ | F |
| Ia28 | Cl | $CH_2C\equiv CH$ | F |
| Ia29 | Cl | $CH_2C\equiv C$—Cl | F |
| Ia30 | Cl | $CH_2C\equiv C$—Br | F |

The tetrahydrophthalimides of formula I according to the invention can be prepared by standard processes of organic chemistry, for example by the following process:

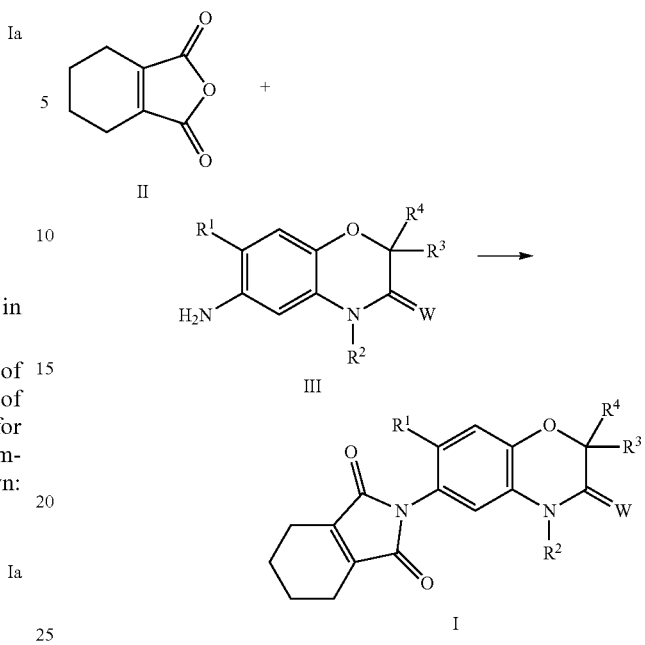

The reaction of the phthalic anhydride II with the amino compound III is usually carried out at from 80° C. to the boiling point of the reaction mixture, preferably at from 80° C. to 200° C., in an inert organic solvent for a period of 1 to 24 hours [EP 170 191].

The phthalic anhydride II is used in an amount of one to three equivalents compared to one equivalent of the amino compound.

Preferred is the amino compound IIIa (=amino compound III wherein $R^4$ is fluorine):

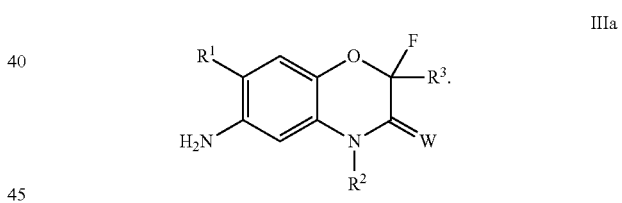

Suitable solvents are aliphatic hydrocarbons such as pentane, hexane, cyclohexane, mixtures of $C_5$-$C_8$-alkanes, heptane and ligroin; aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methylether, dioxane, ethyleneglycol dimethyl ether, anisole and tetrahydrofuran, as well as dimethylsulfoxide, dimethylformamide and N,N-dimethyl-acetamide or N-methylpyrrolidone.

It is also possible to use mixtures of the solvents mentioned.

The reaction mixtures are worked up in a customary manner, for example by mixing with water, separation of the phases and, if appropriate, chromatographic purification of the crude product. Some of the intermediates and end products are obtained in the form of viscous oils, which can be purified or freed from volatile components under reduced pressure and at moderately elevated temperature. If the intermediates and the end products are obtained as solid, purification can also be carried out by recrystallisation or digestion.

The amino compounds III can be obtained from the corresponding nitro compounds IV:

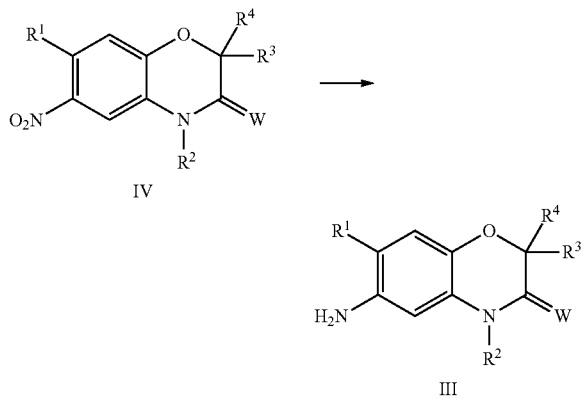

The reduction of the nitro compounds IV is usually carried out at from 20° C. to the boiling point of the reaction mixture, preferably at from 20° C. to 200° C., particularly preferably at from 20° C. to 100° C., in an inert organic solvent [Organikum, Heidelberg, 1993, pages 320-323].

Suitable reducing agents are nascent $H_2$; hydrogen in the presence of catalytic amounts of transition metals or transition metal compounds, in particular those of the 8th transition group, preferably Ni, Pd, Pt, Ru or Rh, either as such, in supported form e.g. supported via activated carbon, Al, $ZrO_2$, $TiO_2$, $SiO_2$, carbonates and the like, or in compounds such as palladium oxide or platinum oxide; or metal hydrides, semimetal hydrides such as aluminium hydride and hydrides derived therefrom such as lithium aluminium hydride, diisobutylaluminiumhydride, borohydrides such as diborane or boranates derived therefrom such as sodium borohydride or lithium borohydride.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, alcohols such as methanol, ethanol, n-propanol, isopropanol, n-butanol and tert.-butanol, Particular preference is given to toluene and methanol. It is also possible to use mixtures of the solvents mentioned.

Work up can be carried out in a known manner.

The nitro compounds IV in turn can be obtained from the corresponding phenyl compounds V:

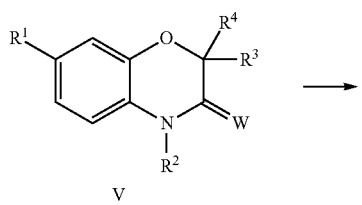

The nitration of the phenyl compound V is usually carried out at from −20° C. to 100° C., particularly preferably at from 0° C. to 20° C. [Organikum, Heidelberg, 1993, pages 553-557].

Suitable nitrating agents are mixtures of $H_2SO_4$ $_{conc}$ and $HNO_3$ $_{conc}$, preferably in a range of 50:1 to 1:50, more preferably 20:1 to 1:20, especially preferred in a range of 10:1 to 1:10.

Work up can be carried out in a known manner.

Those nitro compounds IV, wherein $R^2$ is $C_3$-$C_6$-alkenyl, $C_3$-$C_6$-haloalkenyl, $C_3$-$C_6$-alkynyl or $C_3$-$C_6$-haloalkynyl, preferably $C_3$-$C_6$-alkynyl, can also be prepared by alkylation of nitro compounds IV, wherein $R^2$ is H:

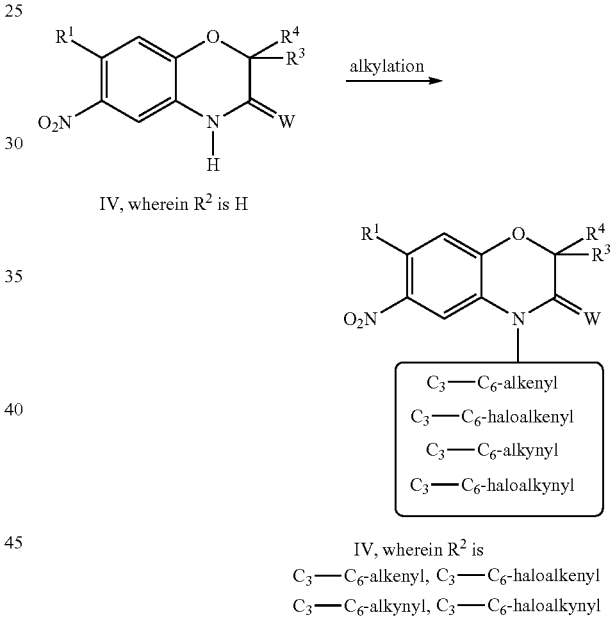

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to ethers such as diethyl ether, diisopropyl ether, tert.-butyl methyl ether, dioxane, anisole and tetrahydrofuran. It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to tertiary amines such as trimethylamine, triethylamine, diisopropylethylamine and alkali metal and alkaline earth metal alkoxides such as sodium methoxide, sodium ethoxide, potassium ethoxide, The bases are generally employed in catalytic amounts; however they can also be employed in equimolar amounts, in excess or, if appropriate, be used as solvent.

Work up can be carried out in a known manner.

The phenyl compounds V in turn can be obtained from the corresponding acetamides VI:

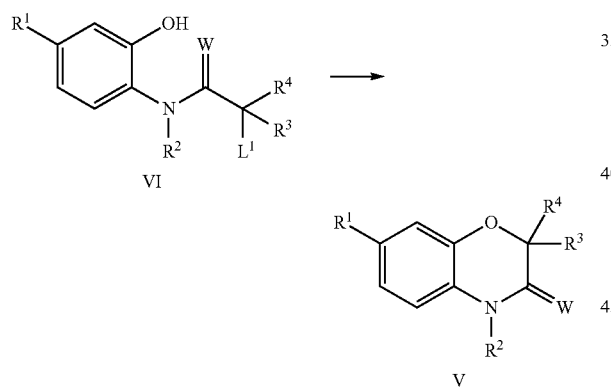

The cyclisation of the acetamide VI is usually carried out at from 0° C. to the boiling point of the reaction mixture, preferably at from 0° C. to 140° C., particularly preferably at from 20° C. to 120° C., in an inert organic solvent in the presence of a base [WO 02/066471].

$L^1$ is halogen selected from Cl, Br, I; preferably Cl or Br; most preferably Cl, also most preferably Br.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, as well as dimethylsulfoxide.

It is also possible to use mixtures of the solvents mentioned.

Suitable bases are, in general Inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines. Particular preference is given to 1,8-Diazabicyclo[5.4.0]undec-7-en (DBU).

The bases are generally employed in catalytic amounts, however they can also be employed in equimolar amounts, in excess or, if appropriate, be used as solvent.

Work up can be carried out in a known manner.

The acetamides VI in turn can be obtained from the corresponding phenol VIII:

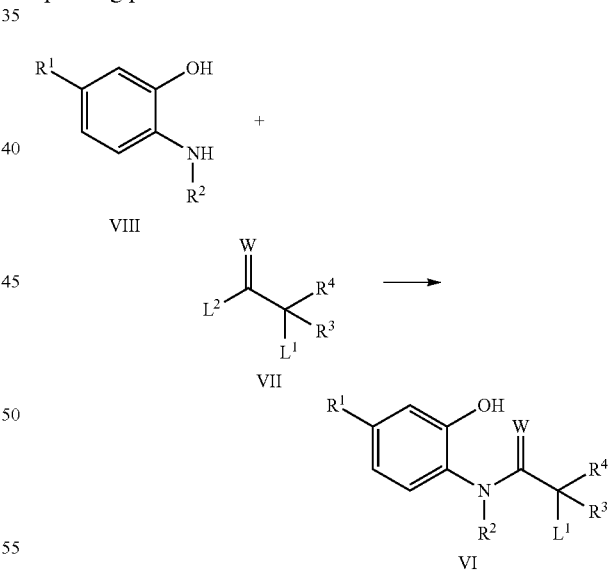

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

$L^1$ is halogen selected from Cl, Br, I; preferably Cl or Br; most preferably Cl, also most preferably Br.

$L^2$ is a known activating group for acylations, e.g. halogen or $C_1$-$C_6$-alkoxy, preferably Cl or $C_1$-$C_6$-alkoxy, most preferably Cl, $OCH_3$ or $OC_2H_5$.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Particular preference is given to tertiary amines such as trimethylamine, triethylamine, diisopropylethylamine and alkali metal and alkaline earth metal alkoxides such as sodium methoxide, sodium ethoxide, potassium ethoxide, The bases are generally employed in catalytic amounts, however they can also be employed in equimolar amounts, in excess or, if appropriate, be used as solvent.

Work up can be carried out in a known manner.

The phenols VIII required for the preparation of the acetamides VI are known from the literature [WO 02/066471] or they can be prepared in accordance with the literature cited and/or are commercially available.

The compounds VII required for the preparation of the acetamides VI are commercially available.

With regard to the educts mentioned for the preparation of the compounds of formula I, the variables mentioned in connection with the educts have the same meaning, preferably the preferred meaning as mentioned herein with regard to the respective variables in formula I.

The tetrahydrophthalimides of formula I are suitable as herbicides. They are suitable as such or as an appropriately formulated composition (herbicidal composition). As used in this application, the terms "formulated composition" and "herbicidal composition" are synonyms. The herbicidal compositions comprising the tetrahydrophthalimides of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the tetrahydrophthalimides of formula I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. altissima, *Beta vulgaris* spec. rapa, *Brassica napus* var. napus, *Brassica napus* var. napobrassica, *Brassica rapa* var. silvestris, *Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (N.rustica), *Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor* (s. vulgare), *Theobroma cacao, Trifolium pratense, Triticum aestivum, Triticale, Triticum durum, Vicia faba, Vitis vinifera* and *Zea mays*.

Preferred crops are the following: *Arachis hypogaea, Beta vulgaris* spec. altissima, *Brassica napus* var. napus, *Brassica oleracea, Citrus limon, Citrus sinensis, Coffea arabica* (Coffea canephora, Coffea liberica), *Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum* (N.rustica), *Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (s. vulgare), Triticale, *Triticum aestivum, Triticum durum, Vicia faba, Vitis vinifera* and *Zea mays*.

The tetrahydrophthalimides of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559, 024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glypho-sate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. Photo-rhab-dus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; aggluti-nins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are dis-closed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton culti-vars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars produ-cing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to in-crease the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato culti-vars, which express resistance genes acting against *Phytophthora infestans* derived from the Mexican wild potato Solanum bulbocastanum) or T4-lyso-zyme (e.g. potato cultivars capable of synthesizing these proteins with increased resistance against bacteria such as *Erwinia amylvora*). The methods for producing such genetically modi-fied plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The tetrahydrophthalimides of formula I according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding.

Suitable are for example crop plants, preferably corn, wheat, sunflower, sugarcane, cotton, rice, canola, oilseed rape or soybeans, which crops are resistant to herbicidal PPO inhibitors, or crop plants which, owing to introduction of the gene for Bt toxin by genetic modification, are resistant to attack by certain insects.

Furthermore, it has been found that the tetrahydrophthalimides of the formula I are also suitable for the defoliation and/or desiccation of plant parts, for which crop plants such as cotton, potato, oilseed rape, sunflower, soybean or field beans, in particular cotton, are suitable. In this regard there have been found compositions for the desiccation and/or defoliation of plants, processes for preparing these compositions and methods for desiccating and/or defoliating plants using the tetrahydrophthalimides of the formula I.

As desiccants, the tetrahydrophthalimides of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval in which the individual cotton plants mature leads to an increased fiber quality after harvesting.

The tetrahydrophthalimides of formula I, or the herbicidal compositions comprising the tetrahydrophthalimides of formula I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one tetrahydrophthalimides of the formula I and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhardt).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thor Chemie and Kathon® MK from Rohm & Haas), and, also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF AG), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF AG, Sokalan types), polyalkoxylates, polyvinylamine (BASF AG, Lupamine types), polyethyleneimine (BASF AG, Lupasol types), polyvinylpyrrolidone and copolymers thereof.

Powders, materials for broadcasting and dusts can be prepared by mixing or concomitant grinding the active ingredients together with a solid carrier. Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water. To prepare emulsions, pastes or oil dispersions, the tetrahydrophthalimides of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the tetrahydrophthalimides of the formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the tetrahydrophthalimides of formula I according to the present invention the active ingredients, e.g. the tetrahydrophthalimides of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The tetrahydrophthalimides of formula I according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The tetrahydrophthalimides of the formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the tetrahydrophthalimides of the formula I or the herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the tetrahydrophthalimides of the formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of the active tetrahydrophthalimides of formula I according to the present invention (total amount of tetrahydrophthalimide I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the tetrahydrophthalimides of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the tetrahydrophthalimides of formula I is 0.1 to 1000 g/ha, preferably 1 to 750 g/ha, more preferably 5 to 500 g/ha, of active substance.

To treat the seed, the tetrahydrophthalimides of formula I are generally employed in amounts of from 0.001 to 10 kg per 100 kg of seed.

To broaden the spectrum of action and to achieve synergistic effects, the tetrahydrophthalimides of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-CF$_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may be beneficial to apply the tetrahydrophthalimides of the formula I alone or in combination with other herbicides, or else in the form of a mixture with other crop protection agents, for example together with agents for controlling pests or phytopathogenic fungi or bacteria.

Also of interest is the miscibility with mineral salt solutions, which are employed for treating nutritional and trace element deficiencies. Other additives such as non-phytotoxic oils and oil concentrates may also be added.

The further herbicidal active component B is preferably selected from the herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

Preference is given to those compositions according to the present invention comprising at least one herbicide B selected from herbicides of class b2, b3, b4, b5, b6, b9 and b10.

Particular preference is given to those compositions according to the present invention which comprise at least one herbicide B selected from the herbicides of class b4, b6 and b10.

Examples of herbicides B which can be used in combination with the tetrahydrophthalimides of the formula I according to the present invention are:
b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofume-sate, flupropanate, molinate, orbencarb, pebulate, prosulfocarb, TCA, thiobencarb, tiocarbazil, triallate and vernolate;
b2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethamet-sulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuronmethyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribacsodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyl-triazolinone herbicides such as flucarbazone, flucarbazone-sodium, propoxycarbazon, propoxycarbazon-sodium, thiencarbazone and thiencarbazone-methyl. Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazin, simazin, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uracils such as bromacil, lenacil and terbacil, and bentazon and bentazon-sodium, pyridate, pyridafol, pentanochlor and propanil and inhibitors of the photosystem I such as diquat, diquatdibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide; among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethyl-phenoxy)-5-methyl-1H-pyrazole-1-carboxamide (CAS 452099-05-7), N-tetrahydro-furfuryl-3-(2-chloro-6-fluoro-4-trifluoromethylphenoxy)-5-methyl-1H-pyrazole-1-carboxamide (CAS 45100-03-7), 3-F-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, and 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione;

b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole, clomazone and flumeturon;

b6) from the group of the EPSP synthase inhibitors:
glyphosate, glyphosate-isopropylammonium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitose inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronilide and napropamide, tetrazolinones such fentrazamide, and other herbicides such as anilofos, cafenstrole, fenoxasulfone, ipfencarbazone, piperophos, pyroxasulfone and isoxazoline compounds of the formula II,

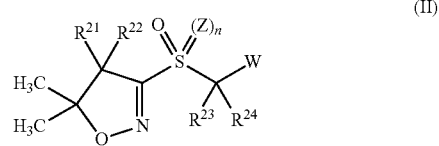

wherein $R^{21}$, $R^{22}$, $R^{23}$, $R^{24}$, W, Z and n have the following meanings:
$R^{21}$, $R^{22}$, $R^{23}$, $R^{24}$ independently of one another hydrogen, halogen or $C_1$-$C_4$-alkyl;

W phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$alkoxy, $C_1$-$C_4$-haloalkyl and $C_1$-$C_4$-haloalkoxy;

preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$;

Z oxygen or NH; and n zero or one;

among the isoxazoline compounds of the formula II, preference is given to isoxazoline compounds of the formula II, wherein $R^{21}$, $R^{22}$, $R^{23}$, $R^{24}$ independently of one another are H, F, Cl or methyl;

Z is oxygen;

n is 0 or 1; and

W is phenyl, pyrazolyl or 1,2,3-triazolyl, wherein the three last-mentioned radicals are unsubstituted or carry one, two or three substituents $R^{yy}$, especially one of the following radicals

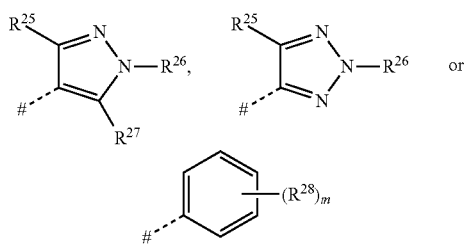

wherein $R^{22}$ is halogen, $C_1$-$C_4$-alkyl or $C_1$-$C_4$-haloalkyl;

$R^{26}$ is $C_1$-$C_4$-alkyl;

$R^{27}$ is halogen, $C_1$-$C_4$-alkoxy or $C_1$-$C_4$-haloalkoxy;

$R^{28}$ is halogen, $C_1$-$C_4$-alkyl, $C_1$-$C_4$-haloalkyl or $C_1$-$C_4$-haloalkoxy;

m is 0, 1, 2 or 3; and # denotes the point of attachment to the group $CR^{23}R^{24}$;

among the isoxazoline compounds of the formula II, particular preference is given to those isoxazoline compounds of the formula II, wherein $R^{21}$ is hydrogen;

$R^{22}$ is fluorine;

$R^{23}$ is hydrogen or fluorine;

$R^{24}$ is hydrogen or fluorine;

W is one of the radicals of the formulae $W^1$, $W^2$, $W^3$ or $W^4$ $W^1$

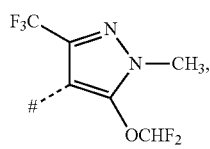

$W^2$

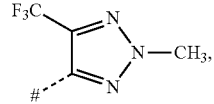

$W^3$

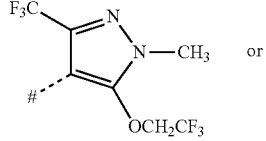

$W^4$

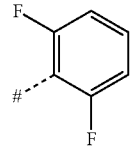

wherein # denotes the point of attachment to the group $CR^{13}R^{14}$;

Z is oxygen;

n is zero or 1, in particular 1; and among these, especially preferred are the isoxazoline compounds of the formulae II.1, II.2, II.3, II.4, II.5, II.6, II.7, II.8 and II.9

II.1

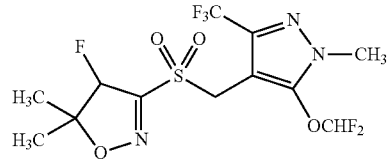

II.2

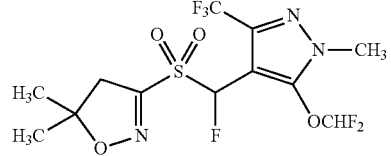

II.3

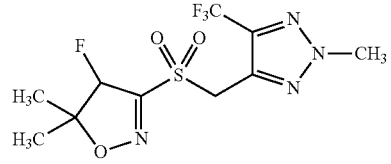

II.4

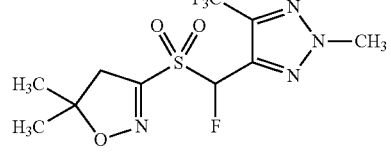

II.5

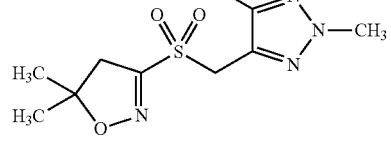

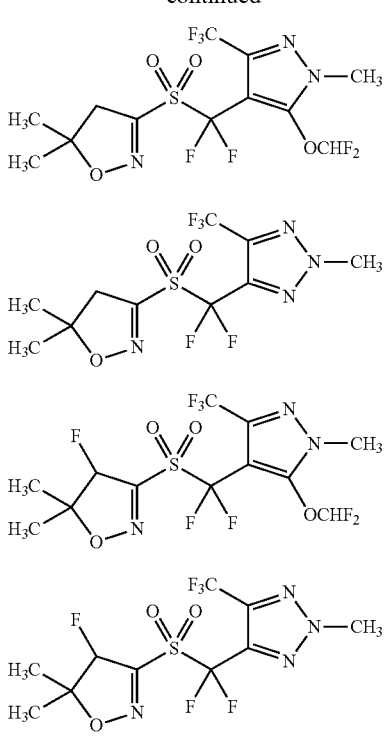

the isoxazoline compounds of the formula II are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, isoxaben, 1-Cyclohexyl-5-pentafluorphenyloxy-1$^4$-[1,2,4,6]thiatriazin-3-ylamine and piperazine compounds of formula III,

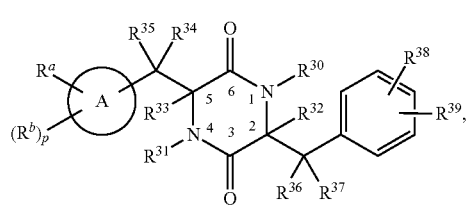

in which

A is phenyl or pyridyl where $R^a$ is attached in the ortho-position to the point of attachment of A to a carbon atom;

$R^a$ is CN, NO$_2$, C$_1$-C$_4$-alkyl, D-C$_3$-C$_6$-cycloalkyl, C$_1$-C$_4$-haloalkyl, C$_1$-C$_4$-alkoxy, C$_1$-C$_4$-haloalkoxy, O-D-C$_3$-C$_6$-cycloalkyl, S(O)$_q$R$^y$, C$_2$-C$_6$-alkenyl, D-C$_3$-C$_6$-cycloalkenyl, C$_3$-C$_6$-alkenyloxy, C$_2$-C$_6$-alkynyl, C$_3$-C$_6$-alkynyloxy, NR$^A$R$^B$, tri-C$_1$-C$_4$-alkylsily, D-C(=O)—R$^{a1}$, D-P(=O)(R$^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa}$ and/or R$^{a1}$, and, if $R^a$ is attached to a carbon atom, additionally halogen;

$R^y$ is C$_1$-C$_6$-alkyl, C$_3$-C$_4$-alkenyl, C$_3$-C$_4$-alkynyl, NR$^A$R$^B$ or C$_1$-C$_4$-haloalkyl and q is 0, 1 or 2;

$R^A$,$R^B$ independently of one another are hydrogen, C$_1$-C$_6$-alkyl, C$_3$-C$_6$-alkenyl and C$_3$-C$_6$-alkynyl; together with the nitrogen atom to which they are attached, $R^A$,$R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups R$^{aa}$;

D is a covalent bond, C$_1$-C$_4$-alkylene, C$_2$-C$_6$-alkenyl or C$_2$-C$_6$-alkynyl;

$R^{a1}$ is hydrogen, OH, C$_1$-C$_8$-Alkyl, C$_1$-C$_4$-haloalkyl, C$_3$-C$_6$-cycloalkyl, C$_2$-C$_8$-alkenyl, C$_5$-C$_6$-cycloalkenyl, C$_2$-C$_8$-alkynyl, C$_1$-C$_6$-alkoxy, C$_1$-C$_4$-haloalkoxy, C$_3$-C$_8$-alkenyloxy, C$_3$-C$_8$-alkynyloxy, NR$^A$R$^B$, C$_1$-C$_6$-alkoxyamino, C$_1$-C$_6$-alkylsulfonylamino, C$_1$-C$_6$-alkylaminosulfonylamino, [di-(C$_1$-C$_6$)alkylamino]sulfonylamino, C$_3$-C$_6$-alkenylamino, C$_3$-C$_6$-alkynylamino, N—(C$_2$-C$_6$-alkenyl)-N-(C$_1$-C$_6$-alkyl)amino, N—(C$_2$-C$_6$-alkynyl)-N—(C$_1$-C$_6$-alkyl)amino, N—(C$_1$-C$_6$-alkoxy)-N—(C$_1$-C$_6$-alkyl)amino, N—(C$_2$-C$_6$-alkenyl)-N—(C$_1$-C$_6$-alkoxy)amino, N—(C$_2$-C$_6$-alkynyl)-N—(C$_1$-C$_6$-alkoxy)amino, C$_1$-C$_6$-alkylsulfonyl, tri-C$_1$-C$_4$-alkylsilyl, phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups R$^{aa}$;

$R^{aa}$ is halogen, OH, CN, NO$_2$, C$_1$-C$_4$-alkyl, C$_1$-C$_4$-haloalkyl, C$_1$-C$_4$-alkoxy, C$_1$-C$_4$-haloalkoxy, S(O)$_q$R$^y$, D-C(=O)—R$^{a1}$ and tri-C$_1$-C$_4$-alkylsilyl;

$R^b$ independently of one another are hydrogen, CN, NO$_2$, halogen, C$_1$-C$_4$-alkyl, C$_1$-C$_4$-haloalkyl, C$_2$-C$_4$-alkenyl, C$_3$-C$_6$-alkynyl, C$_1$-C$_4$-alkoxy, C$_1$-C$_4$-haloalkoxy, benzyl or S(O)$_q$R$^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by R$^{aa}$;

p is 0, 1, 2 or 3;

$R^{30}$ is hydrogen, OH, CN, C$_1$-C$_{12}$-alkyl, C$_3$-C$_{12}$-alkenyl, C$_3$-C$_{12}$-alkynyl, C$_1$-C$_4$-alkoxy, C$_3$-C$_6$-cycloalkyl, C$_5$-C$_6$-cycloalkenyl, NR$^A$R$^B$, S(O)$_n$R$^y$, S(O)$_n$NR$^A$R$^B$, C(=O)R$^{40}$, CONR$^A$R$^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via D$^1$ and are unsubstituted or substituted by 1, 2, 3 or 4 groups R$^{aa}$, and also the following partially or fully R$^{aa}$-substituted groups: C$_1$-C$_4$-alkyl, C$_3$-C$_4$-alkenyl and C$_3$-C$_4$-alkynyl;

$R^{40}$ is hydrogen, C$_1$-C$_4$-alkyl, C$_1$-C$_4$-haloalkyl, C$_1$-C$_4$-alkoxy or C$_1$-C$_4$-haloalkoxy;

D$^1$ is carbonyl or a group D;

where in groups R$^{15}$, $R^a$ and their sub-substituents the carbon chains and/or the cyclic groups may carry 1, 2, 3 or 4 substituents R$^{aa}$ and/or R$^{a1}$;

$R^{31}$ is C$_1$-C$_4$-alkyl, C$_3$-C$_4$-alkenyl or C$_3$-C$_4$-alkynyl;

$R^{32}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or $C(=O)R^{40}$;

$R^{33}$ is hydrogen, halogen, $C_1$-$C_4$-alkyl or $C_1$-$C_4$-haloalkyl, or $R^{33}$ and $R^{34}$ together are a covalent bond;

$R^{34}$, $R^{35}$, $R^{36}$, $R^{37}$ independently of one another are hydrogen, halogen, OH, CN, $NO_2$, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{38}$, $R^{39}$ independently of one another are hydrogen, halogen, OH, haloalkyl, $NR^AR^B$, $NR^AC(O)R^{41}$, CN, $NO_2$, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{41}$, phenoxy or benzyloxy, where in groups $R^{38}$ and $R^{39}$ the carbon chains and/or the cyclic groups may carry 1, 2, 3 or 4 substituents $R^{aa}$;

$R^{41}$ is $C_1$-$C_4$-alkyl or $NR^AR^B$;

among the piperazin compounds of formula III, preference is given to the piperazine compounds of the formula III, wherein A is phenyl or pyridyl where $R^a$ is attached in the ortho-position to the point of attachment of A to a carbon atom;

$R^a$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^AR^B$ or $C_1$-$C_4$-haloalkyl and q is 0, 1 or 2;

$R^A$, $R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A$, $R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_qR^y$, D-C(=O)—$R^{a1}$ and tri-$C_1$-$C_4$-alkylsilyl;

$R^b$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_qR^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{30}$ is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{40}$;

$R^{40}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{30}$, $R^a$ and their sub-substituents the carbon chains and/or the cyclic groups may carry 1, 2, 3 or 4 substituents $R^{aa}$ and/or $R^{a1}$;

$R^{31}$ is $C_1$-$C_4$-alkyl;

$R^{32}$ is OH, $NH_2$, $C_1$-$C_4$-alkyl, $C_3$-$C_6$-cycloalkyl, $C_1$-$C_4$-haloalkyl or $C(=O)R^{25}$;

$R^{33}$ is hydrogen, or $R^{33}$ and $R^{34}$ together are a covalent bond;

$R^{34}$, $R^{35}$, $R^{36}$, $R^{37}$ independently of one another are hydrogen;

$R^{38}$, $R^{39}$ independently of one another are hydrogen, halogen or OH;

b12) from the group of the decoupler herbicides:
dinoseb, dinoterb and DNOC and its salts;

b13) from the group of the auxin herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butometyl, fluoroxypyr-meptyl, MCPA and its salts and esters, MCPA-thioethyl, MCPB and its salts and esters, mecopropand its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors:
diflufenzopyr, diflufenzopyr-sodium, naptalam and naptalam-sodium;

b15) from the group of the other herbicides: bromobutide, chlorflurenol, chlorflurenolmethyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the tetrahydrophthalimides of the formula I in combination with safeners. Safeners are chemical compounds which prevent or reduce damage on useful plants without having a major impact on the herbicidal action of the tetrahydrophthalimides of the formula I towards unwanted plants. They can be applied either before sowings (e.g. on seed treatments, shoots or seedlings) or in the preemergence application or post-emergence application of the useful plant. The safeners and the tetrahydrophthalimides of the formula I can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro

[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds of groups b1) to b15) and the safeners C are known herbicides and safeners, see, for example, The Compendium of Pesticide Common Names (http://www.alanwood.net/pesticides/); B. Hock, C. Fedtke, R. R. Schmidt, Herbizide [Herbicides], Georg Thieme Verlag, Stuttgart, 1995. Further herbicidally active compounds are known from WO 96/26202, WO 97/41116, WO 97/41117, WO 97/41118, WO 01/83459 and WO 2008/074991 and from W. Krämer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one tetrahydrophthalimide of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one tetrahydrophthalimide of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.142 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | diuron |
| B.58 | fluometuron |

TABLE B-continued

| | Herbicide B |
|---|---|
| B.59 | hexazinone |
| B.60 | isoproturon |
| B.61 | linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyl-oxy]acetate (CAS 353292-31-6) |
| B.79 | 3-[7-fluoro-3-oxo-4-(prop-2-ynyl)-3,4-dihydro-2H-benzo[1,4]-oxazin-6-yl]-1,5-dimethyl-6-thioxo-[1,3,5]triazinan-2,4-dione |
| B.80 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione |
| B.81 | benzobicyclon |
| B.82 | clomazone |
| B.83 | diflufenican |
| B.84 | flurochloridone |
| B.85 | isoxaflutole |
| B.86 | mesotrione |
| B.87 | norflurazone |
| B.88 | picolinafen |
| B.89 | sulcotrione |
| B.90 | tefuryltrione |
| B.91 | tembotrione |
| B.92 | topramezone |
| B.93 | bicyclopyrone |
| B.94 | amitrole |
| B.95 | fluometuron |
| B.96 | glyphosate |
| B.97 | glyphosate-isopropylammonium |
| B.98 | glyphosate-trimesium (sulfosate) |
| B.99 | glufosinate |
| B.100 | glufosinate-P |
| B.101 | glufosinate-ammonium |
| B.102 | pendimethalin |
| B.103 | trifluralin |
| B.104 | acetochlor |
| B.105 | butachlor |
| B.106 | cafenstrole |
| B.107 | dimethenamid-P |
| B.108 | fentrazamide |
| B.109 | flufenacet |
| B.110 | mefenacet |
| B.111 | metazachlor |
| B.112 | metolachlor |
| B.113 | S-metolachlor |
| B.114 | pretilachlor |
| B.115 | fenoxasulfone |
| B.116 | isoxaben |
| B.117 | pyroxasulfone |
| B.118 | 2,4-D |
| B.119 | aminopyralid |
| B.120 | clopyralid |
| B.121 | dicamba |
| B.122 | fluroxypyr-meptyl |
| B.123 | MCPA |
| B.124 | quinclorac |
| B.125 | quinmerac |

TABLE B-continued

| | Herbicide B |
|---|---|
| B.126 | aminocyclopyrachlor |
| B.127 | diflufenzopyr |
| B.128 | diflufenzopyr-sodium |
| B.129 | dymron |
| B.130 | indanofan |
| B.131 | indaziflam |
| B.132 | oxaziclomefone |
| B.133 | triaziflam |
| B.134 | II.1 |
| B.135 | II.2 |
| B.136 | II.3 |
| B.137 | II.4 |
| B.138 | II.5 |
| B.139 | II.6 |
| B.140 | II.7 |
| B.141 | II.8 |
| B.142 | II.9 |

Particularly preferred safeners C, which, as component C, are constituent of the composition according to the invention are the safeners C as defined above; in particular the safeners C.1-C.12 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloroacetyl)-1,3-oxazolidine (R-29148, CAS 52836-31-4) |

The weight ratios of the individual components in the preferred mixtures mentioned below are within the limits given above, in particular within the preferred limits.

Particularly preferred are the compositions mentioned below comprising the tetrahydrophthalimides of formula I as defined and the substance(s) as defined in the respective row of table 1;

especially preferred comprising as only herbicidal active compounds the tetrahydro-phthalimides of formula I as defined and the substance(s) as defined in the respective row of table 1;

most preferably comprising as only active compounds the tetrahydrophthalimides of formula I as defined and the substance(s) as defined in the respective row of table 1.

Particularly preferred are compositions 1.1 to 1.1858, comprising the tetrahydro-phthalimide Ia18 and the substance(s) as defined in the respective row of table 1:

TABLE 1

| (compositions 1.1 to 1.1858): | | |
|---|---|---|
| comp. no. | herbicide B | safener C |
| 1.1 | B.1 | — |
| 1.2 | B.2 | — |
| 1.3 | B.3 | — |
| 1.4 | B.4 | — |

TABLE 1-continued (compositions 1.1 to 1.1858):

| comp. no. | herbicide B | safener C |
|---|---|---|
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.1 | C.1 |
| 1.144 | B.2 | C.1 |
| 1.145 | B.3 | C.1 |
| 1.146 | B.4 | C.1 |
| 1.147 | B.5 | C.1 |
| 1.148 | B.6 | C.1 |
| 1.149 | B.7 | C.1 |
| 1.150 | B.8 | C.1 |
| 1.151 | B.9 | C.1 |
| 1.152 | B.10 | C.1 |
| 1.153 | B.11 | C.1 |
| 1.154 | B.12 | C.1 |
| 1.155 | B.13 | C.1 |
| 1.156 | B.14 | C.1 |

TABLE 1-continued (compositions 1.1 to 1.1858):

| comp. no. | herbicide B | safener C |
|---|---|---|
| 1.157 | B.15 | C.1 |
| 1.158 | B.16 | C.1 |
| 1.159 | B.17 | C.1 |
| 1.160 | B.18 | C.1 |
| 1.161 | B.19 | C.1 |
| 1.162 | B.20 | C.1 |
| 1.163 | B.21 | C.1 |
| 1.164 | B.22 | C.1 |
| 1.165 | B.23 | C.1 |
| 1.166 | B.24 | C.1 |
| 1.167 | B.25 | C.1 |
| 1.168 | B.26 | C.1 |
| 1.169 | B.27 | C.1 |
| 1.170 | B.28 | C.1 |
| 1.171 | B.29 | C.1 |
| 1.172 | B.30 | C.1 |
| 1.173 | B.31 | C.1 |
| 1.174 | B.32 | C.1 |
| 1.175 | B.33 | C.1 |
| 1.176 | B.34 | C.1 |
| 1.177 | B.35 | C.1 |
| 1.178 | B.36 | C.1 |
| 1.179 | B.37 | C.1 |
| 1.180 | B.38 | C.1 |
| 1.181 | B.39 | C.1 |
| 1.182 | B.40 | C.1 |
| 1.183 | B.41 | C.1 |
| 1.184 | B.42 | C.1 |
| 1.185 | B.43 | C.1 |
| 1.186 | B.44 | C.1 |
| 1.187 | B.45 | C.1 |
| 1.188 | B.46 | C.1 |
| 1.189 | B.47 | C.1 |
| 1.190 | B.48 | C.1 |
| 1.191 | B.49 | C.1 |
| 1.192 | B.50 | C.1 |
| 1.193 | B.51 | C.1 |
| 1.194 | B.52 | C.1 |
| 1.195 | B.53 | C.1 |
| 1.196 | B.54 | C.1 |
| 1.197 | B.55 | C.1 |
| 1.198 | B.56 | C.1 |
| 1.199 | B.57 | C.1 |
| 1.200 | B.58. | C.1 |
| 1.201 | B.59 | C.1 |
| 1.202 | B.60 | C.1 |
| 1.203 | B.61 | C.1 |
| 1.204 | B.62 | C.1 |
| 1.205 | B.63 | C.1 |
| 1.206 | B.64 | C.1 |
| 1.207 | B.65 | C.1 |
| 1.208 | B.66 | C.1 |
| 1.209 | B.67 | C.1 |
| 1.210 | B.68 | C.1 |
| 1.211 | B.69 | C.1 |
| 1.212 | B.70 | C.1 |
| 1.213 | B.71 | C.1 |
| 1.214 | B.72 | C.1 |
| 1.215 | B.73 | C.1 |
| 1.216 | B.74 | C.1 |
| 1.217 | B.75 | C.1 |
| 1.218 | B.76 | C.1 |
| 1.219 | B.77 | C.1 |
| 1.220 | B.78 | C.1 |
| 1.221 | B.79 | C.1 |
| 1.222 | B.80 | C.1 |
| 1.223 | B.81 | C.1 |
| 1.224 | B.82 | C.1 |
| 1.225 | B.83 | C.1 |
| 1.226 | B.84 | C.1 |
| 1.227 | B.85 | C.1 |
| 1.228 | B.86 | C.1 |
| 1.229 | B.87 | C.1 |
| 1.230 | B.88 | C.1 |
| 1.231 | B.89 | C.1 |
| 1.232 | B.90 | C.1 |
| 1.233 | B.91 | C.1 |
| 1.234 | B.92 | C.1 |
| 1.235 | B.93 | C.1 |
| 1.236 | B.94 | C.1 |
| 1.237 | B.95 | C.1 |
| 1.238 | B.96 | C.1 |
| 1.239 | B.97 | C.1 |
| 1.240 | B.98 | C.1 |
| 1.241 | B.99 | C.1 |
| 1.242 | B.100 | C.1 |
| 1.243 | B.101 | C.1 |
| 1.244 | B.102 | C.1 |
| 1.245 | B.103 | C.1 |
| 1.246 | B.104 | C.1 |
| 1.247 | B.105 | C.1 |
| 1.248 | B.106 | C.1 |
| 1.249 | B.107 | C.1 |
| 1.250 | B.108 | C.1 |
| 1.251 | B.109 | C.1 |
| 1.252 | B.110 | C.1 |
| 1.253 | B.111 | C.1 |
| 1.254 | B.112 | C.1 |
| 1.255 | B.113 | C.1 |
| 1.256 | B.114 | C.1 |
| 1.257 | B.115 | C.1 |
| 1.258 | B.116 | C.1 |
| 1.259 | B.117 | C.1 |
| 1.260 | B.118 | C.1 |
| 1.261 | B.119 | C.1 |
| 1.262 | B.120 | C.1 |
| 1.263 | B.121 | C.1 |
| 1.264 | B.122 | C.1 |
| 1.265 | B.123 | C.1 |
| 1.266 | B.124 | C.1 |
| 1.267 | B.125 | C.1 |
| 1.268 | B.126 | C.1 |
| 1.269 | B.127 | C.1 |
| 1.270 | B.128 | C.1 |
| 1.271 | B.129 | C.1 |
| 1.272 | B.130 | C.1 |
| 1.273 | B.131 | C.1 |
| 1.274 | B.132 | C.1 |
| 1.275 | B.133 | C.1 |
| 1.276 | B.134 | C.1 |
| 1.277 | B.135 | C.1 |
| 1.278 | B.136 | C.1 |
| 1.279 | B.137 | C.1 |
| 1.280 | B.138 | C.1 |
| 1.281 | B.139 | C.1 |
| 1.282 | B.140 | C.1 |
| 1.283 | B.141 | C.1 |
| 1.284 | B.142 | C.1 |
| 1.285 | B.1 | C.2 |
| 1.286 | B.2 | C.2 |
| 1.287 | B.3 | C.2 |
| 1.288 | B.4 | C.2 |
| 1.289 | B.5 | C.2 |
| 1.290 | B.6 | C.2 |
| 1.291 | B.7 | C.2 |
| 1.292 | B.8 | C.2 |
| 1.293 | B.9 | C.2 |
| 1.294 | B.10 | C.2 |
| 1.295 | B.11 | C.2 |
| 1.296 | B.12 | C.2 |
| 1.297 | B.13 | C.2 |
| 1.298 | B.14 | C.2 |
| 1.299 | B.15 | C.2 |
| 1.300 | B.16 | C.2 |
| 1.301 | B.17 | C.2 |
| 1.302 | B.18 | C.2 |
| 1.303 | B.19 | C.2 |
| 1.304 | B.20 | C.2 |
| 1.305 | B.21 | C.2 |
| 1.306 | B.22 | C.2 |
| 1.307 | B.23 | C.2 |
| 1.308 | B.24 | C.2 |

TABLE 1-continued (compositions 1.1 to 1.1858):

| comp. no. | herbicide B | safener C |
|---|---|---|
| 1.309 | B.25 | C.2 |
| 1.310 | B.26 | C.2 |
| 1.311 | B.27 | C.2 |
| 1.312 | B.28 | C.2 |
| 1.313 | B.29 | C.2 |
| 1.314 | B.30 | C.2 |
| 1.315 | B.31 | C.2 |
| 1.316 | B.32 | C.2 |
| 1.317 | B.33 | C.2 |
| 1.318 | B.34 | C.2 |
| 1.319 | B.35 | C.2 |
| 1.320 | B.36 | C.2 |
| 1.321 | B.37 | C.2 |
| 1.322 | B.38 | C.2 |
| 1.323 | B.39 | C.2 |
| 1.324 | B.40 | C.2 |
| 1.325 | B.41 | C.2 |
| 1.326 | B.42 | C.2 |
| 1.327 | B.43 | C.2 |
| 1.328 | B.44 | C.2 |
| 1.329 | B.45 | C.2 |
| 1.330 | B.46 | C.2 |
| 1.331 | B.47 | C.2 |
| 1.332 | B.48 | C.2 |
| 1.333 | B.49 | C.2 |
| 1.334 | B.50 | C.2 |
| 1.335 | B.51 | C.2 |
| 1.336 | B.52 | C.2 |
| 1.337 | B.53 | C.2 |
| 1.338 | B.54 | C.2 |
| 1.339 | B.55 | C.2 |
| 1.340 | B.56 | C.2 |
| 1.341 | B.57 | C.2 |
| 1.342 | B.58 | C.2 |
| 1.343 | B.59 | C.2 |
| 1.344 | B.60 | C.2 |
| 1.345 | B.61 | C.2 |
| 1.346 | B.62 | C.2 |
| 1.347 | B.63 | C.2 |
| 1.348 | B.64 | C.2 |
| 1.349 | B.65 | C.2 |
| 1.350 | B.66 | C.2 |
| 1.351 | B.67 | C.2 |
| 1.352 | B.68 | C.2 |
| 1.353 | B.69 | C.2 |
| 1.354 | B.70 | C.2 |
| 1.355 | B.71 | C.2 |
| 1.356 | B.72 | C.2 |
| 1.357 | B.73 | C.2 |
| 1.358 | B.74 | C.2 |
| 1.359 | B.75 | C.2 |
| 1.360 | B.76 | C.2 |
| 1.361 | B.77 | C.2 |
| 1.362 | B.78 | C.2 |
| 1.363 | B.79 | C.2 |
| 1.364 | B.80 | C.2 |
| 1.365 | B.81 | C.2 |
| 1.366 | B.82 | C.2 |
| 1.367 | B.83 | C.2 |
| 1.368 | B.84 | C.2 |
| 1.369 | B.85 | C.2 |
| 1.370 | B.86 | C.2 |
| 1.371 | B.87 | C.2 |
| 1.372 | B.88 | C.2 |
| 1.373 | B.89 | C.2 |
| 1.374 | B.90 | C.2 |
| 1.375 | B.91 | C.2 |
| 1.376 | B.92 | C.2 |
| 1.377 | B.93 | C.2 |
| 1.378 | B.94 | C.2 |
| 1.379 | B.95 | C.2 |
| 1.380 | B.96 | C.2 |
| 1.381 | B.97 | C.2 |
| 1.382 | B.98 | C.2 |
| 1.383 | B.99 | C.2 |
| 1.384 | B.100 | C.2 |
| 1.385 | B.101 | C.2 |
| 1.386 | B.102 | C.2 |
| 1.387 | B.103 | C.2 |
| 1.388 | B.104 | C.2 |
| 1.389 | B.105 | C.2 |
| 1.390 | B.106 | C.2 |
| 1.391 | B.107 | C.2 |
| 1.392 | B.108 | C.2 |
| 1.393 | B.109 | C.2 |
| 1.394 | B.110 | C.2 |
| 1.395 | B.111 | C.2 |
| 1.396 | B.112 | C.2 |
| 1.397 | B.113 | C.2 |
| 1.398 | B.114 | C.2 |
| 1.399 | B.115 | C.2 |
| 1.400 | B.116 | C.2 |
| 1.401 | B.117 | C.2 |
| 1.402 | B.118 | C.2 |
| 1.403 | B.119 | C.2 |
| 1.404 | B.120 | C.2 |
| 1.405 | B.121 | C.2 |
| 1.406 | B.122 | C.2 |
| 1.407 | B.123 | C.2 |
| 1.408 | B.124 | C.2 |
| 1.409 | B.125 | C.2 |
| 1.410 | B.126 | C.2 |
| 1.411 | B.127 | C.2 |
| 1.412 | B.128 | C.2 |
| 1.413 | B.129 | C.2 |
| 1.414 | B.130 | C.2 |
| 1.415 | B.131 | C.2 |
| 1.416 | B.132 | C.2 |
| 1.417 | B.133 | C.2 |
| 1.418 | B.134 | C.2 |
| 1.419 | B.135 | C.2 |
| 1.420 | B.136 | C.2 |
| 1.421 | B.137 | C.2 |
| 1.422 | B.138 | C.2 |
| 1.423 | B.139 | C.2 |
| 1.424 | B.140 | C.2 |
| 1.425 | B.141 | C.2 |
| 1.426 | B.142 | C.2 |
| 1.427 | B.1 | C.3 |
| 1.428 | B.2 | C.3 |
| 1.429 | B.3 | C.3 |
| 1.430 | B.4 | C.3 |
| 1.431 | B.5 | C.3 |
| 1.432 | B.6 | C.3 |
| 1.433 | B.7 | C.3 |
| 1.434 | B.8 | C.3 |
| 1.435 | B.9 | C.3 |
| 1.436 | B.10 | C.3 |
| 1.437 | B.11 | C.3 |
| 1.438 | B.12 | C.3 |
| 1.439 | B.13 | C.3 |
| 1.440 | B.14 | C.3 |
| 1.441 | B.15 | C.3 |
| 1.442 | B.16 | C.3 |
| 1.443 | B.17 | C.3 |
| 1.444 | B.18 | C.3 |
| 1.445 | B.19 | C.3 |
| 1.446 | B.20 | C.3 |
| 1.447 | B.21 | C.3 |
| 1.448 | B.22 | C.3 |
| 1.449 | B.23 | C.3 |
| 1.450 | B.24 | C.3 |
| 1.451 | B.25 | C.3 |
| 1.452 | B.26 | C.3 |
| 1.453 | B.27 | C.3 |
| 1.454 | B.28 | C.3 |
| 1.455 | B.29 | C.3 |
| 1.456 | B.30 | C.3 |
| 1.457 | B.31 | C.3 |
| 1.458 | B.32 | C.3 |
| 1.459 | B.33 | C.3 |
| 1.460 | B.34 | C.3 |

TABLE 1-continued (compositions 1.1 to 1.1858):

| comp. no. | herbicide B | safener C |
|---|---|---|
| 1.461 | B.35 | C.3 |
| 1.462 | B.36 | C.3 |
| 1.463 | B.37 | C.3 |
| 1.464 | B.38 | C.3 |
| 1.465 | B.39 | C.3 |
| 1.466 | B.40 | C.3 |
| 1.467 | B.41 | C.3 |
| 1.468 | B.42 | C.3 |
| 1.469 | B.43 | C.3 |
| 1.470 | B.44 | C.3 |
| 1.471 | B.45 | C.3 |
| 1.472 | B.46 | C.3 |
| 1.473 | B.47 | C.3 |
| 1.474 | B.48 | C.3 |
| 1.475 | B.49 | C.3 |
| 1.476 | B.50 | C.3 |
| 1.477 | B.51 | C.3 |
| 1.478 | B.52 | C.3 |
| 1.479 | B.53 | C.3 |
| 1.480 | B.54 | C.3 |
| 1.481 | B.55 | C.3 |
| 1.482 | B.56 | C.3 |
| 1.483 | B.57 | C.3 |
| 1.484 | B.58 | C.3 |
| 1.485 | B.59 | C.3 |
| 1.486 | B.60 | C.3 |
| 1.487 | B.61 | C.3 |
| 1.488 | B.62 | C.3 |
| 1.489 | B.63 | C.3 |
| 1.490 | B.64 | C.3 |
| 1.491 | B.65 | C.3 |
| 1.492 | B.66 | C.3 |
| 1.493 | B.67 | C.3 |
| 1.494 | B.68 | C.3 |
| 1.495 | B.69 | C.3 |
| 1.496 | B.70 | C.3 |
| 1.497 | B.71 | C.3 |
| 1.498 | B.72 | C.3 |
| 1.499 | B.73 | C.3 |
| 1.500 | B.74 | C.3 |
| 1.501 | B.75 | C.3 |
| 1.502 | B.76 | C.3 |
| 1.503 | B.77 | C.3 |
| 1.504 | B.78 | C.3 |
| 1.505 | B.79 | C.3 |
| 1.506 | B.80 | C.3 |
| 1.507 | B.81 | C.3 |
| 1.508 | B.82 | C.3 |
| 1.509 | B.83 | C.3 |
| 1.510 | B.84 | C.3 |
| 1.511 | B.85 | C.3 |
| 1.512 | B.86 | C.3 |
| 1.513 | B.87 | C.3 |
| 1.514 | B.88 | C.3 |
| 1.515 | B.89 | C.3 |
| 1.516 | B.90 | C.3 |
| 1.517 | B.91 | C.3 |
| 1.518 | B.92 | C.3 |
| 1.519 | B.93 | C.3 |
| 1.520 | B.94 | C.3 |
| 1.521 | B.95 | C.3 |
| 1.522 | B.96 | C.3 |
| 1.523 | B.97 | C.3 |
| 1.524 | B.98 | C.3 |
| 1.525 | B.99 | C.3 |
| 1.526 | B.100 | C.3 |
| 1.527 | B.101 | C.3 |
| 1.528 | B.102 | C.3 |
| 1.529 | B.103 | C.3 |
| 1.530 | B.104 | C.3 |
| 1.531 | B.105 | C.3 |
| 1.532 | B.106 | C.3 |
| 1.533 | B.107 | C.3 |
| 1.534 | B.108 | C.3 |
| 1.535 | B.109 | C.3 |
| 1.536 | B.110 | C.3 |
| 1.537 | B.111 | C.3 |
| 1.538 | B.112 | C.3 |
| 1.539 | B.113 | C.3 |
| 1.540 | B.114 | C.3 |
| 1.541 | B.115 | C.3 |
| 1.542 | B.116 | C.3 |
| 1.543 | B.117 | C.3 |
| 1.544 | B.118 | C.3 |
| 1.545 | B.119 | C.3 |
| 1.546 | B.120 | C.3 |
| 1.547 | B.121 | C.3 |
| 1.548 | B.122 | C.3 |
| 1.549 | B.123 | C.3 |
| 1.550 | B.124 | C.3 |
| 1.551 | B.125 | C.3 |
| 1.552 | B.126 | C.3 |
| 1.553 | B.127 | C.3 |
| 1.554 | B.128 | C.3 |
| 1.555 | B.129 | C.3 |
| 1.556 | B.130 | C.3 |
| 1.557 | B.131 | C.3 |
| 1.558 | B.132 | C.3 |
| 1.559 | B.133 | C.3 |
| 1.560 | B.134 | C.3 |
| 1.561 | B.135 | C.3 |
| 1.562 | B.136 | C.3 |
| 1.563 | B.137 | C.3 |
| 1.564 | B.138 | C.3 |
| 1.565 | B.139 | C.3 |
| 1.566 | B.140 | C.3 |
| 1.567 | B.141 | C.3 |
| 1.568 | B.142 | C.3 |
| 1.569 | B.1 | C.4 |
| 1.570 | B.2 | C.4 |
| 1.571 | B.3 | C.4 |
| 1.572 | B.4 | C.4 |
| 1.573 | B.5 | C.4 |
| 1.574 | B.6 | C.4 |
| 1.575 | B.7 | C.4 |
| 1.576 | B.8 | C.4 |
| 1.577 | B.9 | C.4 |
| 1.578 | B.10 | C.4 |
| 1.579 | B.11 | C.4 |
| 1.580 | B.12 | C.4 |
| 1.581 | B.13 | C.4 |
| 1.582 | B.14 | C.4 |
| 1.583 | B.15 | C.4 |
| 1.584 | B.16 | C.4 |
| 1.585 | B.17 | C.4 |
| 1.586 | B.18 | C.4 |
| 1.587 | B.19 | C.4 |
| 1.588 | B.20 | C.4 |
| 1.589 | B.21 | C.4 |
| 1.590 | B.22 | C.4 |
| 1.591 | B.23 | C.4 |
| 1.592 | B.24 | C.4 |
| 1.593 | B.25 | C.4 |
| 1.594 | B.26 | C.4 |
| 1.595 | B.27 | C.4 |
| 1.596 | B.28 | C.4 |
| 1.597 | B.29 | C.4 |
| 1.598 | B.30 | C.4 |
| 1.599 | B.31 | C.4 |
| 1.600 | B.32 | C.4 |
| 1.601 | B.33 | C.4 |
| 1.602 | B.34 | C.4 |
| 1.603 | B.35 | C.4 |
| 1.604 | B.36 | C.4 |
| 1.605 | B.37 | C.4 |
| 1.606 | B.38 | C.4 |
| 1.607 | B.39 | C.4 |
| 1.608 | B.40 | C.4 |
| 1.609 | B.41 | C.4 |
| 1.610 | B.42 | C.4 |
| 1.611 | B.43 | C.4 |
| 1.612 | B.44 | C.4 |

TABLE 1-continued (compositions 1.1 to 1.1858):

| comp. no. | herbicide B | safener C |
|---|---|---|
| 1.613 | B.45 | C.4 |
| 1.614 | B.46 | C.4 |
| 1.615 | B.47 | C.4 |
| 1.616 | B.48 | C.4 |
| 1.617 | B.49 | C.4 |
| 1.618 | B.50 | C.4 |
| 1.619 | B.51 | C.4 |
| 1.620 | B.52 | C.4 |
| 1.621 | B.53 | C.4 |
| 1.622 | B.54 | C.4 |
| 1.623 | B.55 | C.4 |
| 1.624 | B.56 | C.4 |
| 1.625 | B.57 | C.4 |
| 1.626 | B.58 | C.4 |
| 1.627 | B.59 | C.4 |
| 1.628 | B.60 | C.4 |
| 1.629 | B.61 | C.4 |
| 1.630 | B.62 | C.4 |
| 1.631 | B.63 | C.4 |
| 1.632 | B.64 | C.4 |
| 1.633 | B.65 | C.4 |
| 1.634 | B.66 | C.4 |
| 1.635 | B.67 | C.4 |
| 1.636 | B.68 | C.4 |
| 1.637 | B.69 | C.4 |
| 1.638 | B.70 | C.4 |
| 1.639 | B.71 | C.4 |
| 1.640 | B.72 | C.4 |
| 1.641 | B.73 | C.4 |
| 1.642 | B.74 | C.4 |
| 1.643 | B.75 | C.4 |
| 1.644 | B.76 | C.4 |
| 1.645 | B.77 | C.4 |
| 1.646 | B.78 | C.4 |
| 1.647 | B.79 | C.4 |
| 1.648 | B.80 | C.4 |
| 1.649 | B.81 | C.4 |
| 1.650 | B.82 | C.4 |
| 1.651 | B.83 | C.4 |
| 1.652 | B.84 | C.4 |
| 1.653 | B.85 | C.4 |
| 1.654 | B.86 | C.4 |
| 1.655 | B.87 | C.4 |
| 1.656 | B.88 | C.4 |
| 1.657 | B.89 | C.4 |
| 1.658 | B.90 | C.4 |
| 1.659 | B.91 | C.4 |
| 1.660 | B.92 | C.4 |
| 1.661 | B.93 | C.4 |
| 1.662 | B.94 | C.4 |
| 1.663 | B.95 | C.4 |
| 1.664 | B.96 | C.4 |
| 1.665 | B.97 | C.4 |
| 1.666 | B.98 | C.4 |
| 1.667 | B.99 | C.4 |
| 1.668 | B.100 | C.4 |
| 1.669 | B.101 | C.4 |
| 1.670 | B.102 | C.4 |
| 1.671 | B.103 | C.4 |
| 1.672 | B.104 | C.4 |
| 1.673 | B.105 | C.4 |
| 1.674 | B.106 | C.4 |
| 1.675 | B.107 | C.4 |
| 1.676 | B.108 | C.4 |
| 1.677 | B.109 | C.4 |
| 1.678 | B.110 | C.4 |
| 1.679 | B.111 | C.4 |
| 1.680 | B.112 | C.4 |
| 1.681 | B.113 | C.4 |
| 1.682 | B.114 | C.4 |
| 1.683 | B.115 | C.4 |
| 1.684 | B.116 | C.4 |
| 1.685 | B.117 | C.4 |
| 1.686 | B.118 | C.4 |
| 1.687 | B.119 | C.4 |
| 1.688 | B.120 | C.4 |
| 1.689 | B.121 | C.4 |
| 1.690 | B.122 | C.4 |
| 1.691 | B.123 | C.4 |
| 1.692 | B.124 | C.4 |
| 1.693 | B.125 | C.4 |
| 1.694 | B.126 | C.4 |
| 1.695 | B.127 | C.4 |
| 1.696 | B.128 | C.4 |
| 1.697 | B.129 | C.4 |
| 1.698 | B.130 | C.4 |
| 1.699 | B.131 | C.4 |
| 1.700 | B.132 | C.4 |
| 1.701 | B.133 | C.4 |
| 1.702 | B.134 | C.4 |
| 1.703 | B.135 | C.4 |
| 1.704 | B.136 | C.4 |
| 1.705 | B.137 | C.4 |
| 1.706 | B.138 | C.4 |
| 1.707 | B.139 | C.4 |
| 1.708 | B.140 | C.4 |
| 1.709 | B.141 | C.4 |
| 1.710 | B.142 | C.4 |
| 1.711 | B.1 | C.5 |
| 1.712 | B.2 | C.5 |
| 1.713 | B.3 | C.5 |
| 1.714 | B.4 | C.5 |
| 1.715 | B.5 | C.5 |
| 1.716 | B.6 | C.5 |
| 1.717 | B.7 | C.5 |
| 1.718 | B.8 | C.5 |
| 1.719 | B.9 | C.5 |
| 1.720 | B.10 | C.5 |
| 1.721 | B.11 | C.5 |
| 1.722 | B.12 | C.5 |
| 1.723 | B.13 | C.5 |
| 1.724 | B.14 | C.5 |
| 1.725 | B.15 | C.5 |
| 1.726 | B.16 | C.5 |
| 1.727 | B.17 | C.5 |
| 1.728 | B.18 | C.5 |
| 1.729 | B.19 | C.5 |
| 1.730 | B.20 | C.5 |
| 1.731 | B.21 | C.5 |
| 1.732 | B.22 | C.5 |
| 1.733 | B.23 | C.5 |
| 1.734 | B.24 | C.5 |
| 1.735 | B.25 | C.5 |
| 1.736 | B.26 | C.5 |
| 1.737 | B.27 | C.5 |
| 1.738 | B.28 | C.5 |
| 1.739 | B.29 | C.5 |
| 1.740 | B.30 | C.5 |
| 1.741 | B.31 | C.5 |
| 1.742 | B.32 | C.5 |
| 1.743 | B.33 | C.5 |
| 1.744 | B.34 | C.5 |
| 1.745 | B.35 | C.5 |
| 1.746 | B.36 | C.5 |
| 1.747 | B.37 | C.5 |
| 1.748 | B.38 | C.5 |
| 1.749 | B.39 | C.5 |
| 1.750 | B.40 | C.5 |
| 1.751 | B.41 | C.5 |
| 1.752 | B.42 | C.5 |
| 1.753 | B.43 | C.5 |
| 1.754 | B.44 | C.5 |
| 1.755 | B.45 | C.5 |
| 1.756 | B.46 | C.5 |
| 1.757 | B.47 | C.5 |
| 1.758 | B.48 | C.5 |
| 1.759 | B.49 | C.5 |
| 1.760 | B.50 | C.5 |
| 1.761 | B.51 | C.5 |
| 1.762 | B.52 | C.5 |
| 1.763 | B.53 | C.5 |
| 1.764 | B.54 | C.5 |

TABLE 1-continued (compositions 1.1 to 1.1858):

| comp. no. | herbicide B | safener C |
|---|---|---|
| 1.765 | B.55 | C.5 |
| 1.766 | B.56 | C.5 |
| 1.767 | B.57 | C.5 |
| 1.768 | B.58 | C.5 |
| 1.769 | B.59 | C.5 |
| 1.770 | B.60 | C.5 |
| 1.771 | B.61 | C.5 |
| 1.772 | B.62 | C.5 |
| 1.773 | B.63 | C.5 |
| 1.774 | B.64 | C.5 |
| 1.775 | B.65 | C.5 |
| 1.776 | B.66 | C.5 |
| 1.777 | B.67 | C.5 |
| 1.778 | B.68 | C.5 |
| 1.779 | B.69 | C.5 |
| 1.780 | B.70 | C.5 |
| 1.781 | B.71 | C.5 |
| 1.782 | B.72 | C.5 |
| 1.783 | B.73 | C.5 |
| 1.784 | B.74 | C.5 |
| 1.785 | B.75 | C.5 |
| 1.786 | B.76 | C.5 |
| 1.787 | B.77 | C.5 |
| 1.788 | B.78 | C.5 |
| 1.789 | B.79 | C.5 |
| 1.790 | B.80 | C.5 |
| 1.791 | B.81 | C.5 |
| 1.792 | B.82 | C.5 |
| 1.793 | B.83 | C.5 |
| 1.794 | B.84 | C.5 |
| 1.795 | B.85 | C.5 |
| 1.796 | B.86 | C.5 |
| 1.797 | B.87 | C.5 |
| 1.798 | B.88 | C.5 |
| 1.799 | B.89 | C.5 |
| 1.800 | B.90 | C.5 |
| 1.801 | B.91 | C.5 |
| 1.802 | B.92 | C.5 |
| 1.803 | B.93 | C.5 |
| 1.804 | B.94 | C.5 |
| 1.805 | B.95 | C.5 |
| 1.806 | B.96 | C.5 |
| 1.807 | B.97 | C.5 |
| 1.808 | B.98 | C.5 |
| 1.809 | B.99 | C.5 |
| 1.810 | B.100 | C.5 |
| 1.811 | B.101 | C.5 |
| 1.812 | B.102 | C.5 |
| 1.813 | B.103 | C.5 |
| 1.814 | B.104 | C.5 |
| 1.815 | B.105 | C.5 |
| 1.816 | B.106 | C.5 |
| 1.817 | B.107 | C.5 |
| 1.818 | B.108 | C.5 |
| 1.819 | B.109 | C.5 |
| 1.820 | B.110 | C.5 |
| 1.821 | B.111 | C.5 |
| 1.822 | B.112 | C.5 |
| 1.823 | B.113 | C.5 |
| 1.824 | B.114 | C.5 |
| 1.825 | B.115 | C.5 |
| 1.826 | B.116 | C.5 |
| 1.827 | B.117 | C.5 |
| 1.828 | B.118 | C.5 |
| 1.829 | B.119 | C.5 |
| 1.830 | B.120 | C.5 |
| 1.831 | B.121 | C.5 |
| 1.832 | B.122 | C.5 |
| 1.833 | B.123 | C.5 |
| 1.834 | B.124 | C.5 |
| 1.835 | B.125 | C.5 |
| 1.836 | B.126 | C.5 |
| 1.837 | B.127 | C.5 |
| 1.838 | B.128 | C.5 |
| 1.839 | B.129 | C.5 |
| 1.840 | B.130 | C.5 |
| 1.841 | B.131 | C.5 |
| 1.842 | B.132 | C.5 |
| 1.843 | B.133 | C.5 |
| 1.844 | B.134 | C.5 |
| 1.845 | B.135 | C.5 |
| 1.846 | B.136 | C.5 |
| 1.847 | B.137 | C.5 |
| 1.848 | B.138 | C.5 |
| 1.849 | B.139 | C.5 |
| 1.850 | B.140 | C.5 |
| 1.851 | B.141 | C.5 |
| 1.852 | B.142 | C.5 |
| 1.853 | B.1 | C.6 |
| 1.854 | B.2 | C.6 |
| 1.855 | B.3 | C.6 |
| 1.856 | B.4 | C.6 |
| 1.857 | B.5 | C.6 |
| 1.858 | B.6 | C.6 |
| 1.859 | B.7 | C.6 |
| 1.860 | B.8 | C.6 |
| 1.861 | B.9 | C.6 |
| 1.862 | B.10 | C.6 |
| 1.863 | B.11 | C.6 |
| 1.864 | B.12 | C.6 |
| 1.865 | B.13 | C.6 |
| 1.866 | B.14 | C.6 |
| 1.867 | B.15 | C.6 |
| 1.868 | B.16 | C.6 |
| 1.869 | B.17 | C.6 |
| 1.870 | B.18 | C.6 |
| 1.871 | B.19 | C.6 |
| 1.872 | B.20 | C.6 |
| 1.873 | B.21 | C.6 |
| 1.874 | B.22 | C.6 |
| 1.875 | B.23 | C.6 |
| 1.876 | B.24 | C.6 |
| 1.877 | B.25 | C.6 |
| 1.878 | B.26 | C.6 |
| 1.879 | B.27 | C.6 |
| 1.880 | B.28 | C.6 |
| 1.881 | B.29 | C.6 |
| 1.882 | B.30 | C.6 |
| 1.883 | B.31 | C.6 |
| 1.884 | B.32 | C.6 |
| 1.885 | B.33 | C.6 |
| 1.886 | B.34 | C.6 |
| 1.887 | B.35 | C.6 |
| 1.888 | B.36 | C.6 |
| 1.889 | B.37 | C.6 |
| 1.890 | B.38 | C.6 |
| 1.891 | B.39 | C.6 |
| 1.892 | B.40 | C.6 |
| 1.893 | B.41 | C.6 |
| 1.894 | B.42 | C.6 |
| 1.895 | B.43 | C.6 |
| 1.896 | B.44 | C.6 |
| 1.897 | B.45 | C.6 |
| 1.898 | B.46 | C.6 |
| 1.899 | B.47 | C.6 |
| 1.900 | B.48 | C.6 |
| 1.901 | B.49 | C.6 |
| 1.902 | B.50 | C.6 |
| 1.903 | B.51 | C.6 |
| 1.904 | B.52 | C.6 |
| 1.905 | B.53 | C.6 |
| 1.906 | B.54 | C.6 |
| 1.907 | B.55 | C.6 |
| 1.908 | B.56 | C.6 |
| 1.909 | B.57 | C.6 |
| 1.910 | B.58. | C.6 |
| 1.911 | B.59 | C.6 |
| 1.912 | B.60 | C.6 |
| 1.913 | B.61 | C.6 |
| 1.914 | B.62 | C.6 |
| 1.915 | B.63 | C.6 |
| 1.916 | B.64 | C.6 |

TABLE 1-continued (compositions 1.1 to 1.1858):

| comp. no. | herbicide B | safener C |
|---|---|---|
| 1.917 | B.65 | C.6 |
| 1.918 | B.66 | C.6 |
| 1.919 | B.67 | C.6 |
| 1.920 | B.68 | C.6 |
| 1.921 | B.69 | C.6 |
| 1.922 | B.70 | C.6 |
| 1.923 | B.71 | C.6 |
| 1.924 | B.72 | C.6 |
| 1.925 | B.73 | C.6 |
| 1.926 | B.74 | C.6 |
| 1.927 | B.75 | C.6 |
| 1.928 | B.76 | C.6 |
| 1.929 | B.77 | C.6 |
| 1.930 | B.78 | C.6 |
| 1.931 | B.79 | C.6 |
| 1.932 | B.80 | C.6 |
| 1.933 | B.81 | C.6 |
| 1.934 | B.82 | C.6 |
| 1.935 | B.83 | C.6 |
| 1.936 | B.84 | C.6 |
| 1.937 | B.85 | C.6 |
| 1.938 | B.86 | C.6 |
| 1.939 | B.87 | C.6 |
| 1.940 | B.88 | C.6 |
| 1.941 | B.89 | C.6 |
| 1.942 | B.90 | C.6 |
| 1.943 | B.91 | C.6 |
| 1.944 | B.92 | C.6 |
| 1.945 | B.93 | C.6 |
| 1.946 | B.94 | C.6 |
| 1.947 | B.95 | C.6 |
| 1.948 | B.96 | C.6 |
| 1.949 | B.97 | C.6 |
| 1.950 | B.98 | C.6 |
| 1.951 | B.99 | C.6 |
| 1.952 | B.100 | C.6 |
| 1.953 | B.101 | C.6 |
| 1.954 | B.102 | C.6 |
| 1.955 | B.103 | C.6 |
| 1.956 | B.104 | C.6 |
| 1.957 | B.105 | C.6 |
| 1.958 | B.106 | C.6 |
| 1.959 | B.107 | C.6 |
| 1.960 | B.108 | C.6 |
| 1.961 | B.109 | C.6 |
| 1.962 | B.110 | C.6 |
| 1.963 | B.111 | C.6 |
| 1.964 | B.112 | C.6 |
| 1.965 | B.113 | C.6 |
| 1.966 | B.114 | C.6 |
| 1.967 | B.115 | C.6 |
| 1.968 | B.116 | C.6 |
| 1.969 | B.117 | C.6 |
| 1.970 | B.118 | C.6 |
| 1.971 | B.119 | C.6 |
| 1.972 | B.120 | C.6 |
| 1.973 | B.121 | C.6 |
| 1.974 | B.122 | C.6 |
| 1.975 | B.123 | C.6 |
| 1.976 | B.124 | C.6 |
| 1.977 | B.125 | C.6 |
| 1.978 | B.126 | C.6 |
| 1.979 | B.127 | C.6 |
| 1.980 | B.128 | C.6 |
| 1.981 | B.129 | C.6 |
| 1.982 | B.130 | C.6 |
| 1.983 | B.131 | C.6 |
| 1.984 | B.132 | C.6 |
| 1.985 | B.133 | C.6 |
| 1.986 | B.134 | C.6 |
| 1.987 | B.135 | C.6 |
| 1.988 | B.136 | C.6 |
| 1.989 | B.137 | C.6 |
| 1.990 | B.138 | C.6 |
| 1.991 | B.139 | C.6 |
| 1.992 | B.140 | C.6 |
| 1.993 | B.141 | C.6 |
| 1.994 | B.142 | C.6 |
| 1.995 | B.1 | C.7 |
| 1.996 | B.2 | C.7 |
| 1.997 | B.3 | C.7 |
| 1.998 | B.4 | C.7 |
| 1.999 | B.5 | C.7 |
| 1.1000 | B.6 | C.7 |
| 1.1001 | B.7 | C.7 |
| 1.1002 | B.8 | C.7 |
| 1.1003 | B.9 | C.7 |
| 1.1004 | B.10 | C.7 |
| 1.1005 | B.11 | C.7 |
| 1.1006 | B.12 | C.7 |
| 1.1007 | B.13 | C.7 |
| 1.1008 | B.14 | C.7 |
| 1.1009 | B.15 | C.7 |
| 1.1010 | B.16 | C.7 |
| 1.1011 | B.17 | C.7 |
| 1.1012 | B.18 | C.7 |
| 1.1013 | B.19 | C.7 |
| 1.1014 | B.20 | C.7 |
| 1.1015 | B.21 | C.7 |
| 1.1016 | B.22 | C.7 |
| 1.1017 | B.23 | C.7 |
| 1.1018 | B.24 | C.7 |
| 1.1019 | B.25 | C.7 |
| 1.1020 | B.26 | C.7 |
| 1.1021 | B.27 | C.7 |
| 1.1022 | B.28 | C.7 |
| 1.1023 | B.29 | C.7 |
| 1.1024 | B.30 | C.7 |
| 1.1025 | B.31 | C.7 |
| 1.1026 | B.32 | C.7 |
| 1.1027 | B.33 | C.7 |
| 1.1028 | B.34 | C.7 |
| 1.1029 | B.35 | C.7 |
| 1.1030 | B.36 | C.7 |
| 1.1031 | B.37 | C.7 |
| 1.1032 | B.38 | C.7 |
| 1.1033 | B.39 | C.7 |
| 1.1034 | B.40 | C.7 |
| 1.1035 | B.41 | C.7 |
| 1.1036 | B.42 | C.7 |
| 1.1037 | B.43 | C.7 |
| 1.1038 | B.44 | C.7 |
| 1.1039 | B.45 | C.7 |
| 1.1040 | B.46 | C.7 |
| 1.1041 | B.47 | C.7 |
| 1.1042 | B.48 | C.7 |
| 1.1043 | B.49 | C.7 |
| 1.1044 | B.50 | C.7 |
| 1.1045 | B.51 | C.7 |
| 1.1046 | B.52 | C.7 |
| 1.1047 | B.53 | C.7 |
| 1.1048 | B.54 | C.7 |
| 1.1049 | B.55 | C.7 |
| 1.1050 | B.56 | C.7 |
| 1.1051 | B.57 | C.7 |
| 1.1052 | B.58. | C.7 |
| 1.1053 | B.59 | C.7 |
| 1.1054 | B.60 | C.7 |
| 1.1055 | B.61 | C.7 |
| 1.1056 | B.62 | C.7 |
| 1.1057 | B.63 | C.7 |
| 1.1058 | B.64 | C.7 |
| 1.1059 | B.65 | C.7 |
| 1.1060 | B.66 | C.7 |
| 1.1061 | B.67 | C.7 |
| 1.1062 | B.68 | C.7 |
| 1.1063 | B.69 | C.7 |
| 1.1064 | B.70 | C.7 |
| 1.1065 | B.71 | C.7 |
| 1.1066 | B.72 | C.7 |
| 1.1067 | B.73 | C.7 |
| 1.1068 | B.74 | C.7 |

TABLE 1-continued (compositions 1.1 to 1.1858):

| comp. no. | herbicide B | safener C |
|---|---|---|
| 1.1069 | B.75 | C.7 |
| 1.1070 | B.76 | C.7 |
| 1.1071 | B.77 | C.7 |
| 1.1072 | B.78 | C.7 |
| 1.1073 | B.79 | C.7 |
| 1.1074 | B.80 | C.7 |
| 1.1075 | B.81 | C.7 |
| 1.1076 | B.82 | C.7 |
| 1.1077 | B.83 | C.7 |
| 1.1078 | B.84 | C.7 |
| 1.1079 | B.85 | C.7 |
| 1.1080 | B.86 | C.7 |
| 1.1081 | B.87 | C.7 |
| 1.1082 | B.88 | C.7 |
| 1.1083 | B.89 | C.7 |
| 1.1084 | B.90 | C.7 |
| 1.1085 | B.91 | C.7 |
| 1.1086 | B.92 | C.7 |
| 1.1087 | B.93 | C.7 |
| 1.1088 | B.94 | C.7 |
| 1.1089 | B.95 | C.7 |
| 1.1090 | B.96 | C.7 |
| 1.1091 | B.97 | C.7 |
| 1.1092 | B.98 | C.7 |
| 1.1093 | B.99 | C.7 |
| 1.1094 | B.100 | C.7 |
| 1.1095 | B.101 | C.7 |
| 1.1096 | B.102 | C.7 |
| 1.1097 | B.103 | C.7 |
| 1.1098 | B.104 | C.7 |
| 1.1099 | B.105 | C.7 |
| 1.1100 | B.106 | C.7 |
| 1.1101 | B.107 | C.7 |
| 1.1102 | B.108 | C.7 |
| 1.1103 | B.109 | C.7 |
| 1.1104 | B.110 | C.7 |
| 1.1105 | B.111 | C.7 |
| 1.1106 | B.112 | C.7 |
| 1.1107 | B.113 | C.7 |
| 1.1108 | B.114 | C.7 |
| 1.1109 | B.115 | C.7 |
| 1.1110 | B.116 | C.7 |
| 1.1111 | B.117 | C.7 |
| 1.1112 | B.118 | C.7 |
| 1.1113 | B.119 | C.7 |
| 1.1114 | B.120 | C.7 |
| 1.1115 | B.121 | C.7 |
| 1.1116 | B.122 | C.7 |
| 1.1117 | B.123 | C.7 |
| 1.1118 | B.124 | C.7 |
| 1.1119 | B.125 | C.7 |
| 1.1120 | B.126 | C.7 |
| 1.1121 | B.127 | C.7 |
| 1.1122 | B.128 | C.7 |
| 1.1123 | B.129 | C.7 |
| 1.1124 | B.130 | C.7 |
| 1.1125 | B.131 | C.7 |
| 1.1126 | B.132 | C.7 |
| 1.1127 | B.133 | C.7 |
| 1.1128 | B.134 | C.7 |
| 1.1129 | B.135 | C.7 |
| 1.1130 | B.136 | C.7 |
| 1.1131 | B.137 | C.7 |
| 1.1132 | B.138 | C.7 |
| 1.1133 | B.139 | C.7 |
| 1.1134 | B.140 | C.7 |
| 1.1135 | B.141 | C.7 |
| 1.1136 | B.142 | C.7 |
| 1.1137 | B.1 | C.8 |
| 1.1138 | B.2 | C.8 |
| 1.1139 | B.3 | C.8 |
| 1.1140 | B.4 | C.8 |
| 1.1141 | B.5 | C.8 |
| 1.1142 | B.6 | C.8 |
| 1.1143 | B.7 | C.8 |
| 1.1144 | B.8 | C.8 |
| 1.1145 | B.9 | C.8 |
| 1.1146 | B.10 | C.8 |
| 1.1147 | B.11 | C.8 |
| 1.1148 | B.12 | C.8 |
| 1.1149 | B.13 | C.8 |
| 1.1150 | B.14 | C.8 |
| 1.1151 | B.15 | C.8 |
| 1.1152 | B.16 | C.8 |
| 1.1153 | B.17 | C.8 |
| 1.1154 | B.18 | C.8 |
| 1.1155 | B.19 | C.8 |
| 1.1156 | B.20 | C.8 |
| 1.1157 | B.21 | C.8 |
| 1.1158 | B.22 | C.8 |
| 1.1159 | B.23 | C.8 |
| 1.1160 | B.24 | C.8 |
| 1.1161 | B.25 | C.8 |
| 1.1162 | B.26 | C.8 |
| 1.1163 | B.27 | C.8 |
| 1.1164 | B.28 | C.8 |
| 1.1165 | B.29 | C.8 |
| 1.1166 | B.30 | C.8 |
| 1.1167 | B.31 | C.8 |
| 1.1168 | B.32 | C.8 |
| 1.1169 | B.33 | C.8 |
| 1.1170 | B.34 | C.8 |
| 1.1171 | B.35 | C.8 |
| 1.1172 | B.36 | C.8 |
| 1.1173 | B.37 | C.8 |
| 1.1174 | B.38 | C.8 |
| 1.1175 | B.39 | C.8 |
| 1.1176 | B.40 | C.8 |
| 1.1177 | B.41 | C.8 |
| 1.1178 | B.42 | C.8 |
| 1.1179 | B.43 | C.8 |
| 1.1180 | B.44 | C.8 |
| 1.1181 | B.45 | C.8 |
| 1.1182 | B.46 | C.8 |
| 1.1183 | B.47 | C.8 |
| 1.1184 | B.48 | C.8 |
| 1.1185 | B.49 | C.8 |
| 1.1186 | B.50 | C.8 |
| 1.1187 | B.51 | C.8 |
| 1.1188 | B.52 | C.8 |
| 1.1189 | B.53 | C.8 |
| 1.1190 | B.54 | C.8 |
| 1.1191 | B.55 | C.8 |
| 1.1192 | B.56 | C.8 |
| 1.1193 | B.57 | C.8 |
| 1.1194 | B.58. | C.8 |
| 1.1195 | B.59 | C.8 |
| 1.1196 | B.60 | C.8 |
| 1.1197 | B.61 | C.8 |
| 1.1198 | B.62 | C.8 |
| 1.1199 | B.63 | C.8 |
| 1.1200 | B.64 | C.8 |
| 1.1201 | B.65 | C.8 |
| 1.1202 | B.66 | C.8 |
| 1.1203 | B.67 | C.8 |
| 1.1204 | B.68 | C.8 |
| 1.1205 | B.69 | C.8 |
| 1.1206 | B.70 | C.8 |
| 1.1207 | B.71 | C.8 |
| 1.1208 | B.72 | C.8 |
| 1.1209 | B.73 | C.8 |
| 1.1210 | B.74 | C.8 |
| 1.1211 | B.75 | C.8 |
| 1.1212 | B.76 | C.8 |
| 1.1213 | B.77 | C.8 |
| 1.1214 | B.78 | C.8 |
| 1.1215 | B.79 | C.8 |
| 1.1216 | B.80 | C.8 |
| 1.1217 | B.81 | C.8 |
| 1.1218 | B.82 | C.8 |
| 1.1219 | B.83 | C.8 |
| 1.1220 | B.84 | C.8 |

TABLE 1-continued (compositions 1.1 to 1.1858):

| comp. no. | herbicide B | safener C |
|---|---|---|
| 1.1221 | B.85 | C.8 |
| 1.1222 | B.86 | C.8 |
| 1.1223 | B.87 | C.8 |
| 1.1224 | B.88 | C.8 |
| 1.1225 | B.89 | C.8 |
| 1.1226 | B.90 | C.8 |
| 1.1227 | B.91 | C.8 |
| 1.1228 | B.92 | C.8 |
| 1.1229 | B.93 | C.8 |
| 1.1230 | B.94 | C.8 |
| 1.1231 | B.95 | C.8 |
| 1.1232 | B.96 | C.8 |
| 1.1233 | B.97 | C.8 |
| 1.1234 | B.98 | C.8 |
| 1.1235 | B.99 | C.8 |
| 1.1236 | B.100 | C.8 |
| 1.1237 | B.101 | C.8 |
| 1.1238 | B.102 | C.8 |
| 1.1239 | B.103 | C.8 |
| 1.1240 | B.104 | C.8 |
| 1.1241 | B.105 | C.8 |
| 1.1242 | B.106 | C.8 |
| 1.1243 | B.107 | C.8 |
| 1.1244 | B.108 | C.8 |
| 1.1245 | B.109 | C.8 |
| 1.1246 | B.110 | C.8 |
| 1.1247 | B.111 | C.8 |
| 1.1248 | B.112 | C.8 |
| 1.1249 | B.113 | C.8 |
| 1.1250 | B.114 | C.8 |
| 1.1251 | B.115 | C.8 |
| 1.1252 | B.116 | C.8 |
| 1.1253 | B.117 | C.8 |
| 1.1254 | B.118 | C.8 |
| 1.1255 | B.119 | C.8 |
| 1.1256 | B.120 | C.8 |
| 1.1257 | B.121 | C.8 |
| 1.1258 | B.122 | C.8 |
| 1.1259 | B.123 | C.8 |
| 1.1260 | B.124 | C.8 |
| 1.1261 | B.125 | C.8 |
| 1.1262 | B.126 | C.8 |
| 1.1263 | B.127 | C.8 |
| 1.1264 | B.128 | C.8 |
| 1.1265 | B.129 | C.8 |
| 1.1266 | B.130 | C.8 |
| 1.1267 | B.131 | C.8 |
| 1.1268 | B.132 | C.8 |
| 1.1269 | B.133 | C.8 |
| 1.1270 | B.134 | C.8 |
| 1.1271 | B.135 | C.8 |
| 1.1272 | B.136 | C.8 |
| 1.1273 | B.137 | C.8 |
| 1.1274 | B.138 | C.8 |
| 1.1275 | B.139 | C.8 |
| 1.1276 | B.140 | C.8 |
| 1.1277 | B.141 | C.8 |
| 1.1278 | B.142 | C.8 |
| 1.1279 | B.1 | C.9 |
| 1.1280 | B.2 | C.9 |
| 1.1281 | B.3 | C.9 |
| 1.1282 | B.4 | C.9 |
| 1.1283 | B.5 | C.9 |
| 1.1284 | B.6 | C.9 |
| 1.1285 | B.7 | C.9 |
| 1.1286 | B.8 | C.9 |
| 1.1287 | B.9 | C.9 |
| 1.1288 | B.10 | C.9 |
| 1.1289 | B.11 | C.9 |
| 1.1290 | B.12 | C.9 |
| 1.1291 | B.13 | C.9 |
| 1.1292 | B.14 | C.9 |
| 1.1293 | B.15 | C.9 |
| 1.1294 | B.16 | C.9 |
| 1.1295 | B.17 | C.9 |
| 1.1296 | B.18 | C.9 |
| 1.1297 | B.19 | C.9 |
| 1.1298 | B.20 | C.9 |
| 1.1299 | B.21 | C.9 |
| 1.1300 | B.22 | C.9 |
| 1.1301 | B.23 | C.9 |
| 1.1302 | B.24 | C.9 |
| 1.1303 | B.25 | C.9 |
| 1.1304 | B.26 | C.9 |
| 1.1305 | B.27 | C.9 |
| 1.1306 | B.28 | C.9 |
| 1.1307 | B.29 | C.9 |
| 1.1308 | B.30 | C.9 |
| 1.1309 | B.31 | C.9 |
| 1.1310 | B.32 | C.9 |
| 1.1311 | B.33 | C.9 |
| 1.1312 | B.34 | C.9 |
| 1.1313 | B.35 | C.9 |
| 1.1314 | B.36 | C.9 |
| 1.1315 | B.37 | C.9 |
| 1.1316 | B.38 | C.9 |
| 1.1317 | B.39 | C.9 |
| 1.1318 | B.40 | C.9 |
| 1.1319 | B.41 | C.9 |
| 1.1320 | B.42 | C.9 |
| 1.1321 | B.43 | C.9 |
| 1.1322 | B.44 | C.9 |
| 1.1323 | B.45 | C.9 |
| 1.1324 | B.46 | C.9 |
| 1.1325 | B.47 | C.9 |
| 1.1326 | B.48 | C.9 |
| 1.1327 | B.49 | C.9 |
| 1.1328 | B.50 | C.9 |
| 1.1329 | B.51 | C.9 |
| 1.1330 | B.52 | C.9 |
| 1.1331 | B.53 | C.9 |
| 1.1332 | B.54 | C.9 |
| 1.1333 | B.55 | C.9 |
| 1.1334 | B.56 | C.9 |
| 1.1335 | B.57 | C.9 |
| 1.1336 | B.58. | C.9 |
| 1.1337 | B.59 | C.9 |
| 1.1338 | B.60 | C.9 |
| 1.1339 | B.61 | C.9 |
| 1.1340 | B.62 | C.9 |
| 1.1341 | B.63 | C.9 |
| 1.1342 | B.64 | C.9 |
| 1.1343 | B.65 | C.9 |
| 1.1344 | B.66 | C.9 |
| 1.1345 | B.67 | C.9 |
| 1.1346 | B.68 | C.9 |
| 1.1347 | B.69 | C.9 |
| 1.1348 | B.70 | C.9 |
| 1.1349 | B.71 | C.9 |
| 1.1350 | B.72 | C.9 |
| 1.1351 | B.73 | C.9 |
| 1.1352 | B.74 | C.9 |
| 1.1353 | B.75 | C.9 |
| 1.1354 | B.76 | C.9 |
| 1.1355 | B.77 | C.9 |
| 1.1356 | B.78 | C.9 |
| 1.1357 | B.79 | C.9 |
| 1.1358 | B.80 | C.9 |
| 1.1359 | B.81 | C.9 |
| 1.1360 | B.82 | C.9 |
| 1.1361 | B.83 | C.9 |
| 1.1362 | B.84 | C.9 |
| 1.1363 | B.85 | C.9 |
| 1.1364 | B.86 | C.9 |
| 1.1365 | B.87 | C.9 |
| 1.1366 | B.88 | C.9 |
| 1.1367 | B.89 | C.9 |
| 1.1368 | B.90 | C.9 |
| 1.1369 | B.91 | C.9 |
| 1.1370 | B.92 | C.9 |
| 1.1371 | B.93 | C.9 |
| 1.1372 | B.94 | C.9 |

TABLE 1-continued (compositions 1.1 to 1.1858):

| comp. no. | herbicide B | safener C |
|---|---|---|
| 1.1373 | B.95 | C.9 |
| 1.1374 | B.96 | C.9 |
| 1.1375 | B.97 | C.9 |
| 1.1376 | B.98 | C.9 |
| 1.1377 | B.99 | C.9 |
| 1.1378 | B.100 | C.9 |
| 1.1379 | B.101 | C.9 |
| 1.1380 | B.102 | C.9 |
| 1.1381 | B.103 | C.9 |
| 1.1382 | B.104 | C.9 |
| 1.1383 | B.105 | C.9 |
| 1.1384 | B.106 | C.9 |
| 1.1385 | B.107 | C.9 |
| 1.1386 | B.108 | C.9 |
| 1.1387 | B.109 | C.9 |
| 1.1388 | B.110 | C.9 |
| 1.1389 | B.111 | C.9 |
| 1.1390 | B.112 | C.9 |
| 1.1391 | B.113 | C.9 |
| 1.1392 | B.114 | C.9 |
| 1.1393 | B.115 | C.9 |
| 1.1394 | B.116 | C.9 |
| 1.1395 | B.117 | C.9 |
| 1.1396 | B.118 | C.9 |
| 1.1397 | B.119 | C.9 |
| 1.1398 | B.120 | C.9 |
| 1.1399 | B.121 | C.9 |
| 1.1400 | B.122 | C.9 |
| 1.1401 | B.123 | C.9 |
| 1.1402 | B.124 | C.9 |
| 1.1403 | B.125 | C.9 |
| 1.1404 | B.126 | C.9 |
| 1.1405 | B.127 | C.9 |
| 1.1406 | B.128 | C.9 |
| 1.1407 | B.129 | C.9 |
| 1.1408 | B.130 | C.9 |
| 1.1409 | B.131 | C.9 |
| 1.1410 | B.132 | C.9 |
| 1.1411 | B.133 | C.9 |
| 1.1412 | B.134 | C.9 |
| 1.1413 | B.135 | C.9 |
| 1.1414 | B.136 | C.9 |
| 1.1415 | B.137 | C.9 |
| 1.1416 | B.138 | C.9 |
| 1.1417 | B.139 | C.9 |
| 1.1418 | B.140 | C.9 |
| 1.1419 | B.141 | C.9 |
| 1.1420 | B.142 | C.9 |
| 1.1421 | B.1 | C.10 |
| 1.1422 | B.2 | C.10 |
| 1.1423 | B.3 | C.10 |
| 1.1424 | B.4 | C.10 |
| 1.1425 | B.5 | C.10 |
| 1.1426 | B.6 | C.10 |
| 1.1427 | B.7 | C.10 |
| 1.1428 | B.8 | C.10 |
| 1.1429 | B.9 | C.10 |
| 1.1430 | B.10 | C.10 |
| 1.1431 | B.11 | C.10 |
| 1.1432 | B.12 | C.10 |
| 1.1433 | B.13 | C.10 |
| 1.1434 | B.14 | C.10 |
| 1.1435 | B.15 | C.10 |
| 1.1436 | B.16 | C.10 |
| 1.1437 | B.17 | C.10 |
| 1.1438 | B.18 | C.10 |
| 1.1439 | B.19 | C.10 |
| 1.1440 | B.20 | C.10 |
| 1.1441 | B.21 | C.10 |
| 1.1442 | B.22 | C.10 |
| 1.1443 | B.23 | C.10 |
| 1.1444 | B.24 | C.10 |
| 1.1445 | B.25 | C.10 |
| 1.1446 | B.26 | C.10 |
| 1.1447 | B.27 | C.10 |
| 1.1448 | B.28 | C.10 |
| 1.1449 | B.29 | C.10 |
| 1.1450 | B.30 | C.10 |
| 1.1451 | B.31 | C.10 |
| 1.1452 | B.32 | C.10 |
| 1.1453 | B.33 | C.10 |
| 1.1454 | B.34 | C.10 |
| 1.1455 | B.35 | C.10 |
| 1.1456 | B.36 | C.10 |
| 1.1457 | B.37 | C.10 |
| 1.1458 | B.38 | C.10 |
| 1.1459 | B.39 | C.10 |
| 1.1460 | B.40 | C.10 |
| 1.1461 | B.41 | C.10 |
| 1.1462 | B.42 | C.10 |
| 1.1463 | B.43 | C.10 |
| 1.1464 | B.44 | C.10 |
| 1.1465 | B.45 | C.10 |
| 1.1466 | B.46 | C.10 |
| 1.1467 | B.47 | C.10 |
| 1.1468 | B.48 | C.10 |
| 1.1469 | B.49 | C.10 |
| 1.1470 | B.50 | C.10 |
| 1.1471 | B.51 | C.10 |
| 1.1472 | B.52 | C.10 |
| 1.1473 | B.53 | C.10 |
| 1.1474 | B.54 | C.10 |
| 1.1475 | B.55 | C.10 |
| 1.1476 | B.56 | C.10 |
| 1.1477 | B.57 | C.10 |
| 1.1478 | B.58. | C.10 |
| 1.1479 | B.59 | C.10 |
| 1.1480 | B.60 | C.10 |
| 1.1481 | B.61 | C.10 |
| 1.1482 | B.62 | C.10 |
| 1.1483 | B.63 | C.10 |
| 1.1484 | B.64 | C.10 |
| 1.1485 | B.65 | C.10 |
| 1.1486 | B.66 | C.10 |
| 1.1487 | B.67 | C.10 |
| 1.1488 | B.68 | C.10 |
| 1.1489 | B.69 | C.10 |
| 1.1490 | B.70 | C.10 |
| 1.1491 | B.71 | C.10 |
| 1.1492 | B.72 | C.10 |
| 1.1493 | B.73 | C.10 |
| 1.1494 | B.74 | C.10 |
| 1.1495 | B.75 | C.10 |
| 1.1496 | B.76 | C.10 |
| 1.1497 | B.77 | C.10 |
| 1.1498 | B.78 | C.10 |
| 1.1499 | B.79 | C.10 |
| 1.1500 | B.80 | C.10 |
| 1.1501 | B.81 | C.10 |
| 1.1502 | B.82 | C.10 |
| 1.1503 | B.83 | C.10 |
| 1.1504 | B.84 | C.10 |
| 1.1505 | B.85 | C.10 |
| 1.1506 | B.86 | C.10 |
| 1.1507 | B.87 | C.10 |
| 1.1508 | B.88 | C.10 |
| 1.1509 | B.89 | C.10 |
| 1.1510 | B.90 | C.10 |
| 1.1511 | B.91 | C.10 |
| 1.1512 | B.92 | C.10 |
| 1.1513 | B.93 | C.10 |
| 1.1514 | B.94 | C.10 |
| 1.1515 | B.95 | C.10 |
| 1.1516 | B.96 | C.10 |
| 1.1517 | B.97 | C.10 |
| 1.1518 | B.98 | C.10 |
| 1.1519 | B.99 | C.10 |
| 1.1520 | B.100 | C.10 |
| 1.1521 | B.101 | C.10 |
| 1.1522 | B.102 | C.10 |
| 1.1523 | B.103 | C.10 |
| 1.1524 | B.104 | C.10 |

TABLE 1-continued (compositions 1.1 to 1.1858):

| comp. no. | herbicide B | safener C |
|---|---|---|
| 1.1525 | B.105 | C.10 |
| 1.1526 | B.106 | C.10 |
| 1.1527 | B.107 | C.10 |
| 1.1528 | B.108 | C.10 |
| 1.1529 | B.109 | C.10 |
| 1.1530 | B.110 | C.10 |
| 1.1531 | B.111 | C.10 |
| 1.1532 | B.112 | C.10 |
| 1.1533 | B.113 | C.10 |
| 1.1534 | B.114 | C.10 |
| 1.1535 | B.115 | C.10 |
| 1.1536 | B.116 | C.10 |
| 1.1537 | B.117 | C.10 |
| 1.1538 | B.118 | C.10 |
| 1.1539 | B.119 | C.10 |
| 1.1540 | B.120 | C.10 |
| 1.1541 | B.121 | C.10 |
| 1.1542 | B.122 | C.10 |
| 1.1543 | B.123 | C.10 |
| 1.1544 | B.124 | C.10 |
| 1.1545 | B.125 | C.10 |
| 1.1546 | B.126 | C.10 |
| 1.1547 | B.127 | C.10 |
| 1.1548 | B.128 | C.10 |
| 1.1549 | B.129 | C.10 |
| 1.1550 | B.130 | C.10 |
| 1.1551 | B.131 | C.10 |
| 1.1552 | B.132 | C.10 |
| 1.1553 | B.133 | C.10 |
| 1.1554 | B.134 | C.10 |
| 1.1555 | B.135 | C.10 |
| 1.1556 | B.136 | C.10 |
| 1.1557 | B.137 | C.10 |
| 1.1558 | B.138 | C.10 |
| 1.1559 | B.139 | C.10 |
| 1.1560 | B.140 | C.10 |
| 1.1561 | B.141 | C.10 |
| 1.1562 | B.142 | C.10 |
| 1.1563 | B.1 | C.11 |
| 1.1564 | B.2 | C.11 |
| 1.1565 | B.3 | C.11 |
| 1.1566 | B.4 | C.11 |
| 1.1567 | B.5 | C.11 |
| 1.1568 | B.6 | C.11 |
| 1.1569 | B.7 | C.11 |
| 1.1570 | B.8 | C.11 |
| 1.1571 | B.9 | C.11 |
| 1.1572 | B.10 | C.11 |
| 1.1573 | B.11 | C.11 |
| 1.1574 | B.12 | C.11 |
| 1.1575 | B.13 | C.11 |
| 1.1576 | B.14 | C.11 |
| 1.1577 | B.15 | C.11 |
| 1.1578 | B.16 | C.11 |
| 1.1579 | B.17 | C.11 |
| 1.1580 | B.18 | C.11 |
| 1.1581 | B.19 | C.11 |
| 1.1582 | B.20 | C.11 |
| 1.1583 | B.21 | C.11 |
| 1.1584 | B.22 | C.11 |
| 1.1585 | B.23 | C.11 |
| 1.1586 | B.24 | C.11 |
| 1.1587 | B.25 | C.11 |
| 1.1588 | B.26 | C.11 |
| 1.1589 | B.27 | C.11 |
| 1.1590 | B.28 | C.11 |
| 1.1591 | B.29 | C.11 |
| 1.1592 | B.30 | C.11 |
| 1.1593 | B.31 | C.11 |
| 1.1594 | B.32 | C.11 |
| 1.1595 | B.33 | C.11 |
| 1.1596 | B.34 | C.11 |
| 1.1597 | B.35 | C.11 |
| 1.1598 | B.36 | C.11 |
| 1.1599 | B.37 | C.11 |
| 1.1600 | B.38 | C.11 |
| 1.1601 | B.39 | C.11 |
| 1.1602 | B.40 | C.11 |
| 1.1603 | B.41 | C.11 |
| 1.1604 | B.42 | C.11 |
| 1.1605 | B.43 | C.11 |
| 1.1606 | B.44 | C.11 |
| 1.1607 | B.45 | C.11 |
| 1.1608 | B.46 | C.11 |
| 1.1609 | B.47 | C.11 |
| 1.1610 | B.48 | C.11 |
| 1.1611 | B.49 | C.11 |
| 1.1612 | B.50 | C.11 |
| 1.1613 | B.51 | C.11 |
| 1.1614 | B.52 | C.11 |
| 1.1615 | B.53 | C.11 |
| 1.1616 | B.54 | C.11 |
| 1.1617 | B.55 | C.11 |
| 1.1618 | B.56 | C.11 |
| 1.1619 | B.57 | C.11 |
| 1.1620 | B.58. | C.11 |
| 1.1621 | B.59 | C.11 |
| 1.1622 | B.60 | C.11 |
| 1.1623 | B.61 | C.11 |
| 1.1624 | B.62 | C.11 |
| 1.1625 | B.63 | C.11 |
| 1.1626 | B.64 | C.11 |
| 1.1627 | B.65 | C.11 |
| 1.1628 | B.66 | C.11 |
| 1.1629 | B.67 | C.11 |
| 1.1630 | B.68 | C.11 |
| 1.1631 | B.69 | C.11 |
| 1.1632 | B.70 | C.11 |
| 1.1633 | B.71 | C.11 |
| 1.1634 | B.72 | C.11 |
| 1.1635 | B.73 | C.11 |
| 1.1636 | B.74 | C.11 |
| 1.1637 | B.75 | C.11 |
| 1.1638 | B.76 | C.11 |
| 1.1639 | B.77 | C.11 |
| 1.1640 | B.78 | C.11 |
| 1.1641 | B.79 | C.11 |
| 1.1642 | B.80 | C.11 |
| 1.1643 | B.81 | C.11 |
| 1.1644 | B.82 | C.11 |
| 1.1645 | B.83 | C.11 |
| 1.1646 | B.84 | C.11 |
| 1.1647 | B.85 | C.11 |
| 1.1648 | B.86 | C.11 |
| 1.1649 | B.87 | C.11 |
| 1.1650 | B.88 | C.11 |
| 1.1651 | B.89 | C.11 |
| 1.1652 | B.90 | C.11 |
| 1.1653 | B.91 | C.11 |
| 1.1654 | B.92 | C.11 |
| 1.1655 | B.93 | C.11 |
| 1.1656 | B.94 | C.11 |
| 1.1657 | B.95 | C.11 |
| 1.1658 | B.96 | C.11 |
| 1.1659 | B.97 | C.11 |
| 1.1660 | B.98 | C.11 |
| 1.1661 | B.99 | C.11 |
| 1.1662 | B.100 | C.11 |
| 1.1663 | B.101 | C.11 |
| 1.1664 | B.102 | C.11 |
| 1.1665 | B.103 | C.11 |
| 1.1666 | B.104 | C.11 |
| 1.1667 | B.105 | C.11 |
| 1.1668 | B.106 | C.11 |
| 1.1669 | B.107 | C.11 |
| 1.1670 | B.108 | C.11 |
| 1.1671 | B.109 | C.11 |
| 1.1672 | B.110 | C.11 |
| 1.1673 | B.111 | C.11 |
| 1.1674 | B.112 | C.11 |
| 1.1675 | B.113 | C.11 |
| 1.1676 | B.114 | C.11 |

TABLE 1-continued (compositions 1.1 to 1.1858):

| comp. no. | herbicide B | safener C |
|---|---|---|
| 1.1677 | B.115 | C.11 |
| 1.1678 | B.116 | C.11 |
| 1.1679 | B.117 | C.11 |
| 1.1680 | B.118 | C.11 |
| 1.1681 | B.119 | C.11 |
| 1.1682 | B.120 | C.11 |
| 1.1683 | B.121 | C.11 |
| 1.1684 | B.122 | C.11 |
| 1.1685 | B.123 | C.11 |
| 1.1686 | B.124 | C.11 |
| 1.1687 | B.125 | C.11 |
| 1.1688 | B.126 | C.11 |
| 1.1689 | B.127 | C.11 |
| 1.1690 | B.128 | C.11 |
| 1.1691 | B.129 | C.11 |
| 1.1692 | B.130 | C.11 |
| 1.1693 | B.131 | C.11 |
| 1.1694 | B.132 | C.11 |
| 1.1695 | B.133 | C.11 |
| 1.1696 | B.134 | C.11 |
| 1.1697 | B.135 | C.11 |
| 1.1698 | B.136 | C.11 |
| 1.1699 | B.137 | C.11 |
| 1.1700 | B.138 | C.11 |
| 1.1701 | B.139 | C.11 |
| 1.1702 | B.140 | C.11 |
| 1.1703 | B.141 | C.11 |
| 1.1704 | B.142 | C.11 |
| 1.1705 | B.1 | C.12 |
| 1.1706 | B.2 | C.12 |
| 1.1707 | B.3 | C.12 |
| 1.1708 | B.4 | C.12 |
| 1.1709 | B.5 | C.12 |
| 1.1710 | B.6 | C.12 |
| 1.1711 | B.7 | C.12 |
| 1.1712 | B.8 | C.12 |
| 1.1713 | B.9 | C.12 |
| 1.1714 | B.10 | C.12 |
| 1.1715 | B.11 | C.12 |
| 1.1716 | B.12 | C.12 |
| 1.1717 | B.13 | C.12 |
| 1.1718 | B.14 | C.12 |
| 1.1719 | B.15 | C.12 |
| 1.1720 | B.16 | C.12 |
| 1.1721 | B.17 | C.12 |
| 1.1722 | B.18 | C.12 |
| 1.1723 | B.19 | C.12 |
| 1.1724 | B.20 | C.12 |
| 1.1725 | B.21 | C.12 |
| 1.1726 | B.22 | C.12 |
| 1.1727 | B.23 | C.12 |
| 1.1728 | B.24 | C.12 |
| 1.1729 | B.25 | C.12 |
| 1.1730 | B.26 | C.12 |
| 1.1731 | B.27 | C.12 |
| 1.1732 | B.28 | C.12 |
| 1.1733 | B.29 | C.12 |
| 1.1734 | B.30 | C.12 |
| 1.1735 | B.31 | C.12 |
| 1.1736 | B.32 | C.12 |
| 1.1737 | B.33 | C.12 |
| 1.1738 | B.34 | C.12 |
| 1.1739 | B.35 | C.12 |
| 1.1740 | B.36 | C.12 |
| 1.1741 | B.37 | C.12 |
| 1.1742 | B.38 | C.12 |
| 1.1743 | B.39 | C.12 |
| 1.1744 | B.40 | C.12 |
| 1.1745 | B.41 | C.12 |
| 1.1746 | B.42 | C.12 |
| 1.1747 | B.43 | C.12 |
| 1.1748 | B.44 | C.12 |
| 1.1749 | B.45 | C.12 |
| 1.1750 | B.46 | C.12 |
| 1.1751 | B.47 | C.12 |
| 1.1752 | B.48 | C.12 |
| 1.1753 | B.49 | C.12 |
| 1.1754 | B.50 | C.12 |
| 1.1755 | B.51 | C.12 |
| 1.1756 | B.52 | C.12 |
| 1.1757 | B.53 | C.12 |
| 1.1758 | B.54 | C.12 |
| 1.1759 | B.55 | C.12 |
| 1.1760 | B.56 | C.12 |
| 1.1761 | B.57 | C.12 |
| 1.1762 | B.58. | C.12 |
| 1.1763 | B.59 | C.12 |
| 1.1764 | B.60 | C.12 |
| 1.1765 | B.61 | C.12 |
| 1.1766 | B.62 | C.12 |
| 1.1767 | B.63 | C.12 |
| 1.1768 | B.64 | C.12 |
| 1.1769 | B.65 | C.12 |
| 1.1770 | B.66 | C.12 |
| 1.1771 | B.67 | C.12 |
| 1.1772 | B.68 | C.12 |
| 1.1773 | B.69 | C.12 |
| 1.1774 | B.70 | C.12 |
| 1.1775 | B.71 | C.12 |
| 1.1776 | B.72 | C.12 |
| 1.1777 | B.73 | C.12 |
| 1.1778 | B.74 | C.12 |
| 1.1779 | B.75 | C.12 |
| 1.1780 | B.76 | C.12 |
| 1.1781 | B.77 | C.12 |
| 1.1782 | B.78 | C.12 |
| 1.1783 | B.79 | C.12 |
| 1.1784 | B.80 | C.12 |
| 1.1785 | B.81 | C.12 |
| 1.1786 | B.82 | C.12 |
| 1.1787 | B.83 | C.12 |
| 1.1788 | B.84 | C.12 |
| 1.1789 | B.85 | C.12 |
| 1.1790 | B.86 | C.12 |
| 1.1791 | B.87 | C.12 |
| 1.1792 | B.88 | C.12 |
| 1.1793 | B.89 | C.12 |
| 1.1794 | B.90 | C.12 |
| 1.1795 | B.91 | C.12 |
| 1.1796 | B.92 | 0.12 |
| 1.1797 | B.93 | C.12 |
| 1.1798 | B.94 | C.12 |
| 1.1799 | B.95 | C.12 |
| 1.1800 | B.96 | C.12 |
| 1.1801 | B.97 | C.12 |
| 1.1802 | B.98 | C.12 |
| 1.1803 | B.99 | C.12 |
| 1.1804 | B.100 | C.12 |
| 1.1805 | B.101 | C.12 |
| 1.1806 | B.102 | C.12 |
| 1.1807 | B.103 | C.12 |
| 1.1808 | B.104 | C.12 |
| 1.1809 | B.105 | C.12 |
| 1.1810 | B.106 | C.12 |
| 1.1811 | B.107 | C.12 |
| 1.1812 | B.108 | C.12 |
| 1.1813 | B.109 | C.12 |
| 1.1814 | B.110 | C.12 |
| 1.1815 | B.111 | C.12 |
| 1.1816 | B.112 | C.12 |
| 1.1817 | B.113 | C.12 |
| 1.1818 | B.114 | C.12 |
| 1.1819 | B.115 | C.12 |
| 1.1820 | B.116 | C.12 |
| 1.1821 | B.117 | C.12 |
| 1.1822 | B.118 | C.12 |
| 1.1823 | B.119 | C.12 |
| 1.1824 | B.120 | C.12 |
| 1.1825 | B.121 | C.12 |
| 1.1826 | B.122 | C.12 |
| 1.1827 | B.123 | C.12 |
| 1.1828 | B.124 | C.12 |

TABLE 1-continued (compositions 1.1 to 1.1858):

| comp. no. | herbicide B | safener C |
|---|---|---|
| 1.1829 | B.125 | C.12 |
| 1.1830 | B.126 | C.12 |
| 1.1831 | B.127 | C.12 |
| 1.1832 | B.128 | C.12 |
| 1.1833 | B.129 | C.12 |
| 1.1834 | B.130 | C.12 |
| 1.1835 | B.131 | C.12 |
| 1.1836 | B.132 | C.12 |
| 1.1837 | B.133 | C.12 |
| 1.1838 | B.134 | C.12 |
| 1.1839 | B.135 | C.12 |
| 1.1840 | B.136 | C.12 |
| 1.1841 | B.137 | C.12 |
| 1.1842 | B.138 | C.12 |
| 1.1843 | B.139 | C.12 |
| 1.1844 | B.140 | C.12 |
| 1.1845 | B.141 | C.12 |
| 1.1846 | B.142 | C.12 |
| 1.1847 | — | C.1 |
| 1.1848 | — | C.2 |
| 1.1849 | — | C.3 |
| 1.1850 | — | C.4 |
| 1.1851 | — | C.5 |
| 1.1852 | — | C.6 |
| 1.1853 | — | C.7 |
| 1.1854 | — | C.8 |
| 1.1855 | — | C.9 |
| 1.1856 | — | C.10 |
| 1.1857 | — | C.11 |
| 1.1858 | — | C.12 |

The specific number for each single composition is deductible as follows:

Composition 1.777 for example comprises the tetrahydrophthalimide Ia18, terbutryn (B.67) and fenchlorazole (C.5) (see table 1, entry 1.777; as well as table B, entry B.67 and table C, entry C.5).

Composition 2.777 for example comprises the tetrahydrophthalimide Ia1 (see the definition for compositions 2.1 to 2.1858 below), terbutryn (B.67) and fenchlorazole (C.5) (see table 1, entry 1.777; as well as table B, entry B.67 and table C, entry C.5).

Composition 7.777 for example comprises imazapyr (B31) (see the definition for compositions 7.1 to 7.1858 below), and the tetrahydrophthalimide Ia18, terbutryn (B.67) and fenchlorazole (C.5) (see table 1, entry 1.777; as well as table B, entry B.67 and table C, entry C.5).

Also especially preferred are compositions 2.1. to 2.1858 which differ from the corresponding compositions 1.1 to 1.1858 only in that they comprise as the active compound A the tetrahydrophthalimide Ia1.

Also especially preferred are compositions 3.1. to 3.1858 which differ from the corresponding compositions 1.1 to 1.1858 only in that they additionally comprise B.2 as further herbicide B.

Also especially preferred are compositions 4.1. to 4.1858 which differ from the corresponding compositions 1.1 to 1.1858 only in that they additionally comprise B.7 as further herbicide B.

Also especially preferred are compositions 5.1. to 5.1858 which differ from the corresponding compositions 1.1 to 1.1858 only in that they additionally comprise B.29 as further herbicide B.

Also especially preferred are compositions 6.1. to 6.1858 which differ from the corresponding compositions 1.1 to 1.1858 only in that they additionally comprise B.30 as further herbicide B.

Also especially preferred are compositions 7.1. to 7.1858 which differ from the corresponding compositions 1.1 to 1.1858 only in that they additionally comprise B.31 as further herbicide B.

Also especially preferred are compositions 8.1. to 8.1858 which differ from the corresponding compositions 1.1 to 1.1858 only in that they additionally comprise B.32 as further herbicide B.

Also especially preferred are compositions 9.1. to 9.1858 which differ from the corresponding compositions 1.1 to 1.1858 only in that they additionally comprise B.33 as further herbicide B.

Also especially preferred are compositions 10.1. to 10.1858 which differ from the corresponding compositions 1.1 to 1.1858 only in that they additionally comprise B.40 as further herbicide B.

Also especially preferred are compositions 11.1. to 11.1858 which differ from the corresponding compositions 1.1 to 1.1858 only in that they additionally comprise B.44 as further herbicide B.

Also especially preferred are compositions 12.1. to 12.1858 which differ from the corresponding compositions 1.1 to 1.1858 only in that they additionally comprise B.45 as further herbicide B.

Also especially preferred are compositions 13.1. to 13.1858 which differ from the corresponding compositions 1.1 to 1.1858 only in that they additionally comprise B.52 as further herbicide B.

Also especially preferred are compositions 14.1. to 14.1858 which differ from the corresponding compositions 1.1 to 1.1858 only in that they additionally comprise B.53 as further herbicide B.

Also especially preferred are compositions 15.1. to 15.1858 which differ from the corresponding compositions 1.1 to 1.1858 only in that they additionally comprise B.54 as further herbicide B.

Also especially preferred are compositions 16.1. to 16.1858 which differ from the corresponding compositions 1.1 to 1.1858 only in that they additionally comprise B.55 as further herbicide B.

Also especially preferred are compositions 17.1. to 17.1858 which differ from the corresponding compositions 1.1 to 1.1858 only in that they additionally comprise B.56 as further herbicide B.

Also especially preferred are compositions 18.1. to 18.1858 which differ from the corresponding compositions 1.1 to 1.1858 only in that they additionally comprise B.57 as further herbicide B.

Also especially preferred are compositions 19.1. to 19.1858 which differ from the corresponding compositions 1.1 to 1.1858 only in that they additionally comprise B.60 as further herbicide B.

Also especially preferred are compositions 20.1. to 20.1858 which differ from the corresponding compositions 1.1 to 1.1858 only in that they additionally comprise B.65 as further herbicide B.

Also especially preferred are compositions 21.1. to 21.1858 which differ from the corresponding compositions 1.1 to 1.1858 only in that they additionally comprise B.66 as further herbicide B.

Also especially preferred are compositions 22.1. to 22.1858 which differ from the corresponding compositions 1.1 to 1.1858 only in that they additionally comprise B.69 as further herbicide B.

Also especially preferred are compositions 23.1. to 23.1858 which differ from the corresponding compositions 1.1 to 1.1858 only in that they additionally comprise B.72 as further herbicide B.

Also especially preferred are compositions 24.1. to 24.1858 which differ from the corresponding compositions 1.1 to 1.1858 only in that they additionally comprise B.73 as further herbicide B.

Also especially preferred are compositions 25.1. to 25.1858 which differ from the corresponding compositions 1.1 to 1.1858 only in that they additionally comprise B.76 as further herbicide B.

Also especially preferred are compositions 26.1. to 26.1858 which differ from the corresponding compositions 1.1 to 1.1858 only in that they additionally comprise B.77 as further herbicide B.

Also especially preferred are compositions 27.1. to 27.1858 which differ from the corresponding compositions 1.1 to 1.1858 only in that they additionally comprise B.81 as further herbicide B.

Also especially preferred are compositions 28.1. to 28.1858 which differ from the corresponding compositions 1.1 to 1.1858 only in that they additionally comprise B.82 as further herbicide B.

Also especially preferred are compositions 29.1. to 29.1858 which differ from the corresponding compositions 1.1 to 1.1858 only in that they additionally comprise B.85 as further herbicide B.

Also especially preferred are compositions 30.1. to 30.1858 which differ from the corresponding compositions 1.1 to 1.1858 only in that they additionally comprise B.85 and B.54 as further herbicides B.

Also especially preferred are compositions 31.1. to 31.1858 which differ from the corresponding compositions 1.1 to 1.1858 only in that they additionally comprise B.85 and B.60 as further herbicides B.

Also especially preferred are compositions 32.1. to 32.1858 which differ from the corresponding compositions 1.1 to 1.1858 only in that they additionally comprise B.85 and B.66 as further herbicides B.

Also especially preferred are compositions 33.1. to 33.1858 which differ from the corresponding compositions 1.1 to 1.1858 only in that they additionally comprise B. 86 as further herbicide B.

Also especially preferred are compositions 34.1. to 34.1858 which differ from the corresponding compositions 1.1 to 1.1858 only in that they additionally comprise B. 86 and B.54 as further herbicides B.

Also especially preferred are compositions 35.1. to 35.1858 which differ from the corresponding compositions 1.1 to 1.1858 only in that they additionally comprise B. 86 and B.60 as further herbicides B.

Also especially preferred are compositions 36.1. to 36.1858 which differ from the corresponding compositions 1.1 to 1.1858 only in that they additionally comprise B. 86 and B.66 as further herbicides B.

Also especially preferred are compositions 37.1. to 37.1858 which differ from the corresponding compositions 1.1 to 1.1858 only in that they additionally comprise B.88 as further herbicide B.

Also especially preferred are compositions 38.1. to 38.1858 which differ from the corresponding compositions 1.1 to 1.1858 only in that they additionally comprise B. 89 as further herbicide B.

Also especially preferred are compositions 39.1. to 39.1858 which differ from the corresponding compositions 1.1 to 1.1858 only in that they additionally comprise B. 89 and B.54 as further herbicides B.

Also especially preferred are compositions 40.1. to 40.1858 which differ from the corresponding compositions 1.1 to 1.1858 only in that they additionally comprise B. 89 and B.60 as further herbicides B.

Also especially preferred are compositions 41.1. to 41.1858 which differ from the corresponding compositions 1.1 to 1.1858 only in that they additionally comprise B. 89 and B.66 as further herbicides B.

Also especially preferred are compositions 42.1. to 42.1858 which differ from the corresponding compositions 1.1 to 1.1858 only in that they additionally comprise B.91 as further herbicide B.

Also especially preferred are compositions 43.1. to 43.1858 which differ from the corresponding compositions 1.1 to 1.1858 only in that they additionally comprise B.92 as further herbicide B.

Also especially preferred are compositions 44.1. to 44.1858 which differ from the corresponding compositions 1.1 to 1.1858 only in that they additionally comprise B.92 and B.54 as further herbicides B.

Also especially preferred are compositions 45.1. to 45.1858 which differ from the corresponding compositions 1.1 to 1.1858 only in that they additionally comprise B.92 and B.60 as further herbicides B.

Also especially preferred are compositions 46.1. to 46.1858 which differ from the corresponding compositions 1.1 to 1.1858 only in that they additionally comprise B.92 and B.66 as further herbicides B.

Also especially preferred are compositions 47.1. to 47.1858 which differ from the corresponding compositions 1.1 to 1.1858 only in that they additionally comprise B.96 as further herbicide B.

Also especially preferred are compositions 48.1. to 48.1858 which differ from the corresponding compositions 1.1 to 1.1858 only in that they additionally comprise B.96 and B.54 as further herbicides B.

Also especially preferred are compositions 49.1. to 49.1858 which differ from the corresponding compositions 1.1 to 1.1858 only in that they additionally comprise B.96 and B.76 as further herbicides B.

Also especially preferred are compositions 50.1. to 50.1858 which differ from the corresponding compositions 1.1 to 1.1858 only in that they additionally comprise B.96 and B.85 as further herbicides B.

Also especially preferred are compositions 51.1. to 51.1858 which differ from the corresponding compositions 1.1 to 1.1858 only in that they additionally comprise B.96 and 8.104 as further herbicides B.

Also especially preferred are compositions 52.1. to 52.1858 which differ from the corresponding compositions 1.1 to 1.1858 only in that they additionally comprise B.96 and B.86 as further herbicides B.

Also especially preferred are compositions 53.1. to 53.1858 which differ from the corresponding compositions 1.1 to 1.1858 only in that they additionally comprise B.96 and B.89 as further herbicides B.

Also especially preferred are compositions 54.1. to 54.1858 which differ from the corresponding compositions 1.1 to 1.1858 only in that they additionally comprise B.96 and B.92 as further herbicides B.

Also especially preferred are compositions 55.1. to 55.1858 which differ from the corresponding compositions 1.1 to 1.1858 only in that they additionally comprise B.99 as further herbicide B.

Also especially preferred are compositions 56.1. to 56.1858 which differ from the corresponding compositions 1.1 to 1.1858 only in that they additionally comprise 8.102 as further herbicide B.

Also especially preferred are compositions 57.1. to 57.1858 which differ from the corresponding compositions 1.1 to 1.1858 only in that they additionally comprise B.104 as further herbicide B.

Also especially preferred are compositions 58.1. to 58.1858 which differ from the corresponding compositions 1.1 to 1.1858 only in that they additionally comprise B.107 as further herbicide B.

Also especially preferred are compositions 59.1. to 59.1858 which differ from the corresponding compositions 1.1 to 1.1858 only in that they additionally comprise B.108 as further herbicide B.

Also especially preferred are compositions 60.1. to 60.1858 which differ from the corresponding compositions 1.1 to 1.1858 only in that they additionally comprise B.109 as further herbicide B.

Also especially preferred are compositions 61.1. to 61.1858 which differ from the corresponding compositions 1.1 to 1.1858 only in that they additionally comprise B.111 as further herbicide B.

Also especially preferred are compositions 62.1. to 62.1858 which differ from the corresponding compositions 1.1 to 1.1858 only in that they additionally comprise B.113 as further herbicide B.

Also especially preferred are compositions 63.1. to 63.1858 which differ from the corresponding compositions 11.1 to 1.1858 only in that they additionally comprise B.114 as further herbicide B.

Also especially preferred are compositions 64.1. to 64.1858 which differ from the corresponding compositions 1.1 to 1.1858 only in that they additionally comprise B.118 as further herbicide B.

Also especially preferred are compositions 65.1. to 65.1858 which differ from the corresponding compositions 1.1 to 1.1858 only in that they additionally comprise B.120 as further herbicide B.

Also especially preferred are compositions 66.1. to 66.1858 which differ from the corresponding compositions 1.1 to 1.1858 only in that they additionally comprise B.121 as further herbicide B.

Also especially preferred are compositions 67.1. to 67.1858 which differ from the corresponding compositions 1.1 to 1.1858 only in that they additionally comprise B.123 as further herbicide B.

Also especially preferred are compositions 68.1. to 68.1858 which differ from the corresponding compositions 1.1 to 1.1858 only in that they additionally comprise B.124 as further herbicide B.

Also especially preferred are compositions 69.1. to 69.1858 which differ from the corresponding compositions 1.1 to 1.1858 only in that they additionally comprise B.131 as further herbicide B.

Hereinbelow, the preparation of the tetrahydrophthalimides of the formula I is illustrated by examples; however, the subject matter of the present invention is not limited to the examples given.

EXAMPLE 1

2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione (Ia18)

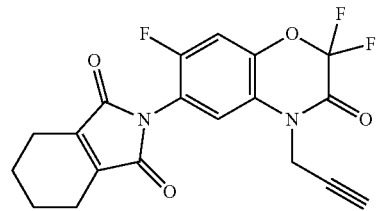 [SMILES: C#CCN1C(=O)C(F)(F)Oc2cc(F)c(N3C(=O)C4=C(CCCC4)C3=O)cc21]

6-amino-2,2,7-trifluoro-4-(prop-2-ynyl)-2H-benzo[b][1,4]oxazin-3(4H)-one (20 g, 78 mmol) and 4,5,6,7-tetrahydroisobenzofuran-1,3-dione (12.47 g, 82 mmol) in acetic acid (500 ml) were stirred at 120° C. overnight, after which time tlc (thin layer chromatography) analysis indicated that the reaction was complete. The reaction mixture was concentrated in vacuo and triturated with toluene to yield 34.6 g of crude product. This material was combined with a further quantity (6.23 g) of crude product which had been obtained in a similar manner, and the combined product was coated on isolute absorbens (~70 g). Filtration over silica afforded 2 fractions: F1: 12.9 g and F2: 19.35 g. Both fractions were triturated with di-isopropyl ether to yield: T1: 6.04 g (88% purity) and T2: 14.7 g (>95% purity). T1 was recrystallised from MeOH to yield a further 4.65 g of product (>95% purity).

$^1$H NMR: δ (DMSO) 7.73 (1H, d), 7.64 (1H, d), 4.78 (2H, s), 3.34 (1H, s), 2.37 (4H, br s), 1.75 (4H, br s).

Use Examples

The herbicidal activity of the tetrahydrophthalimides of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific name | Common name |
|---|---|---|
| ABUTH | *Abutilon theophrasti* | velvetleaf |
| AMARE | *Amaranthus retroflexus* | common amaranth |
| AMBEL | *Ambrosia elatior* | common ragweed |
| BRAPL | *Brachiaria plantaginea* | alexandergrass |
| CHEAL | *Chenopodium album* | lambsquarters |
| DIGSA | *Digitaria sanguinales* | large crabgrass |
| ECHCG | *Echinocloa crus-galli* | comon barnyardgrass |
| ERICA | *Erigeron canadensis* | Canada horseweed |
| LAMAM | *Lamium amplexicaule* | henbit |
| PANDI | *Panicum dichotomiflorun* | fall panicum |
| PHBPU | *Pharbitis purpurea* | common morning glory |
| SETFA | *Setaria faberi* | Faber's foxtail |
| SETVI | *Setaria viridis* | green foxtail |
| STEME | *Stellaria media* | Common chickweed |

At an application rate of 6.25 g/ha, the compound Ia18 applied by the post-emergence method, showed very good herbicidal activity against *Abutilon theophrasti, Ambrosia elatior, Chenopodium album* and *Pharbitis purpurea*.

At an application rate of 6.25 g/ha, the compound Ia18 applied by the pre-emergence method, showed very good herbicidal activity against *Amaranthus retroflexus* and *Erigeron canadensis*.

TABLE 2

Synergistic herbicidal action of the mixture 1.30 applied by the post-emergence method

| application rate a.s. in g/ha | | herbicidal activity against | | | |
|---|---|---|---|---|---|
| | | BRAPL | | DIGSA | |
| Ia18 | B.30 | found | calculated | found | calculated |
| 6.25 | — | 25 | — | 20 | — |
| — | 10 | 70 | — | 85 | — |
| 6.25 | 10 | 80 | 78 | 95 | 88 |

TABLE 3

Synergistic herbicidal action of the mixture 1.76 applied by the pre-emergence method

| application rate a.s. in g/ha | | herbicidal activity against | | | |
|---|---|---|---|---|---|
| | | PANDI | | ABUTH | |
| Ia18 | B.76 | found | calculated | found | calculated |
| 12.5 | — | 70 | — | 55 | — |
| — | 6.25 | 55 | — | 75 | — |
| 12.5 | 6.25 | 98 | 87 | 100 | 89 |

TABLE 4

Synergistic herbicidal action of the mixture 1.76 applied by the post-emergence method

| application rate a.s. in g/ha | | herbicidal activity against | | | |
|---|---|---|---|---|---|
| | | SETFA | | SETVI | |
| Ia18 | B.76 | found | calculated | found | calculated |
| 6.25 | — | 70 | — | 55 | — |
| — | 12.5 | 30 | — | 40 | — |
| 6.25 | 12.5 | 90 | 79 | 80 | 73 |

TABLE 5

Synergistic herbicidal action of the mixture 1.97 applied by the post-emergence method

| application rate a.s. in g/ha | | herbicidal activity against ECHCG | |
|---|---|---|---|
| Ia18 | B.97 | found | calculated |
| 6.25 | — | 30 | — |
| — | 135 | 85 | — |
| 6.25 | 135 | 95 | 90 |

TABLE 6

Synergistic herbicidal action of the mixture 1.102 applied by the pre-emergence method

| application rate a.s. in g/ha | | herbicidal activity against STEME | |
|---|---|---|---|
| Ia18 | B.102 | found | calculated |
| 13 | — | 65 | — |
| — | 400 | 75 | — |
| 13 | 400 | 100 | 91 |

TABLE 7

Synergistic herbicidal action of the mixture 1.107 applied by the pre-emergence method

| application rate a.s. in g/ha | | herbicidal activity against | | | |
|---|---|---|---|---|---|
| | | SETVI | | PANDI | |
| Ia18 | B.107 | found | calculated | found | calculated |
| 25 | — | 90 | — | 95 | — |
| — | 15 | 70 | — | 95 | — |
| 25 | 15 | 100 | 97 | 100 | 100 |

TABLE 8

| Synergistic herbicidal action of the mixture 1.117 applied by the pre-emergence method | | | | | |
|---|---|---|---|---|---|
| application rate a.s. in g/ha | | herbicidal activity against | | | |
| | | LAMAM | | STEME | |
| Ia18 | B.117 | found | calculated | found | calculated |
| 12.5 | — | 80 | — | 65 | — |
| — | 6.25 | 35 | — | 60 | — |
| 12.5 | 6.25 | 100 | 87 | 100 | 86 |

The invention claimed is:

1. A compound of formula Ia

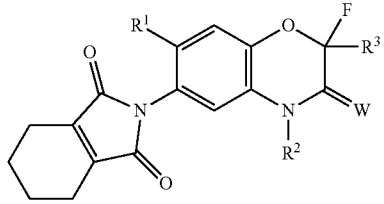

wherein
R$^1$ is hydrogen or halogen;
R$^2$ is hydrogen, C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl;
R$^3$ is halogen; and
W is O or S.

2. The compound of claim 1, wherein R$^1$ is halogen.

3. The compound of claim 1, wherein R$^3$ is F.

4. The compound of claim 1, wherein R$^2$ is C$_3$-C$_6$-alkynyl or C$_3$-C$_6$-haloalkynyl.

5. A process for preparing the compound of claim 1, comprising reacting a compound of formula II

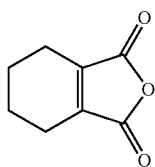

with a compound of formula IIIa

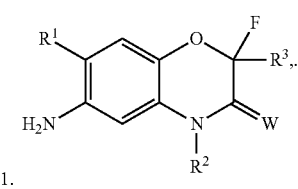

6. A herbicidal composition comprising a herbicidal active amount of a compound of claim 1 and at least one further active compound.

7. The herbicidal composition of claim 6, further comprising an inert liquid and/or solid carrier and, optionally, a surfactant.

8. The composition according to claim 6 comprising two active compounds selected from the group of the herbicides B consisting of:
b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;
b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters
and/or safeners C selected from the group consisting of
(quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diary)-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives.

9. The herbicidal composition of claim 8, further comprising an inert liquid and/or solid carrier and, optionally, a surfactant.

10. A method of controlling undesired vegetation, which comprises allowing a herbicidal active amount of a compound of claim 1 to act on plants, their environment or on seed.

11. The method of 10, wherein R$^1$ of the compound of formula Ia is halogen.

12. The method of 10, wherein R$^3$ of the compound of formula Ia is F.

13. The method of 10, wherein R$^2$ of the compound of formula Ia is C$_3$-C$_6$-alkynyl or C$_3$-C$_6$-haloalkynyl.

14. A method of controlling undesired vegetation, which comprises allowing the herbicidal active composition of claim 6 to act on plants, their environment or on seed.

15. The method of claim 14, wherein the composition further comprises an inert liquid and/or solid carrier and, optionally, at least one surface-active substance.

16. The method of claim 15, wherein the composition further comprises two active compounds from the group of the herbicides B and/or safeners C.

17. The method of claim 16, wherein the composition further comprises an inert liquid and/or solid carrier and, optionally, at least one surface-active substance.

18. The method of 17, wherein $R^1$ of the compound of formula Ia is halogen.

19. The method of 17, wherein $R^3$ of the compound of formula Ia is F.

20. The method of 17, wherein $R^2$ of the compound of formula Ia is $C_3$-$C_6$-alkynyl or $C_3$-$C_6$-haloalkynyl.

* * * * *

UNITED STATES PATENT AND TRADEMARK OFFICE
CERTIFICATE OF CORRECTION

PATENT NO. : 8,445,407 B2  
APPLICATION NO. : 13/505106  
DATED : May 21, 2013  
INVENTOR(S) : Matthias Witschel et al.

Page 1 of 1

It is certified that error appears in the above-identified patent and that said Letters Patent is hereby corrected as shown below:

In the Claims

Col. 66, claim 8, lines 42-43, delete "4,5-dihydro-5,5-diary)-3-isoxazol carboxylic acids" and insert therefore --4,5-dihydro-5,5-diaryl-3-isoxazol carboxylic acids--

Signed and Sealed this  
Twenty-eighth Day of January, 2014

Michelle K. Lee  
*Deputy Director of the United States Patent and Trademark Office*